(12) United States Patent
von Lehe et al.

(10) Patent No.: US 10,537,418 B2
(45) Date of Patent: *Jan. 21, 2020

(54) RAPID EXCHANGE CATHETERS AND EMBOLIC PROTECTION DEVICES

(71) Applicant: Covidien LP, Mansfield, MA (US)

(72) Inventors: Cathleen von Lehe, Rogers, MN (US); Sengkham Sirivong, Big Lake, MN (US)

(73) Assignee: Covidien LP, Mansfield, MA (US)

( * ) Notice: Subject to any disclaimer, the term of this patent is extended or adjusted under 35 U.S.C. 154(b) by 486 days.

This patent is subject to a terminal disclaimer.

(21) Appl. No.: 15/252,502

(22) Filed: Aug. 31, 2016

(65) Prior Publication Data

US 2017/0049551 A1    Feb. 23, 2017

Related U.S. Application Data

(63) Continuation of application No. 13/149,464, filed on May 31, 2011, now Pat. No. 9,456,889, which is a
(Continued)

(51) Int. Cl.
  *A61F 2/01* (2006.01)
  *A61M 25/01* (2006.01)
  (Continued)

(52) U.S. Cl.
  CPC ........ *A61F 2/013* (2013.01); *A61B 17/12022* (2013.01); *A61B 17/12109* (2013.01);
  (Continued)

(58) Field of Classification Search
  CPC .... A61F 2/01; A61F 2/013; A61F 2230/0067; A61F 2002/018; A61F 2230/0008;
  (Continued)

(56) References Cited

U.S. PATENT DOCUMENTS 3,297,030 A    1/1967  Czorny et al.
3,595,241 A    7/1971  Sheridan
(Continued)

FOREIGN PATENT DOCUMENTS

EP    0350043 A1    1/1990
EP    0350043 B1    1/1990
(Continued)

OTHER PUBLICATIONS

US 6,348,062 B1, 02/2002, Hopkins et al. (withdrawn)
(Continued)

*Primary Examiner* — Elizabeth Houston
*Assistant Examiner* — Michael G Mendoza

(57) ABSTRACT

A catheter compiling a housing portion defining an interior cavity and the housing portion comprising a housing member having an interior space dimensioned for housing an indwelling medical device. The elongated member comprises a lumen extending at least from an exit port to a distal port, the housing member is disposed within the lumen, and the lumen is dimensioned in the housing portion to receive a guidewire outside of the interior space of the housing member. A medical device for filtering emboli from blood flowing in a blood vessel of patient comprising an elongate support member and an elongate side branch member connected to the elongate support member. The filter element is attached to the elongate side branch member by a proximal filter element slider, and the elongate side branch member is adapted to maintain the filter element centered in the vessel.

27 Claims, 23 Drawing Sheets

Related U.S. Application Data continuation of application No. 11/357,404, filed on Feb. 17, 2006, now Pat. No. 7,955,351.

(60) Provisional application No. 60/654,389, filed on Feb. 18, 2005.

(51) Int. Cl.
*A61B 17/12* (2006.01)
*A61M 25/00* (2006.01)

(52) U.S. Cl.
CPC .. *A61B 17/12122* (2013.01); *A61B 17/12172* (2013.01); *A61F 2/01* (2013.01); *A61M 25/0023* (2013.01); *A61B 2017/1205* (2013.01); *A61F 2002/011* (2013.01); *A61F 2002/015* (2013.01); *A61F 2002/016* (2013.01); *A61F 2002/018* (2013.01); *A61F 2230/0008* (2013.01); *A61F 2230/0067* (2013.01); *A61M 2025/0183* (2013.01)

(58) Field of Classification Search
CPC ......... A61F 2002/015; A61F 2002/011; A61B 17/12022; A61B 17/12172; A61B 17/12122; A61B 17/12109; A61B 2017/1205; A61M 2025/0183; A61M 25/0023
See application file for complete search history.

(56) References Cited

U.S. PATENT DOCUMENTS

| | | |
|---|---|---|
| 4,306,562 A | 12/1981 | Osborne |
| 4,425,908 A | 1/1984 | Simon |
| 4,552,554 A | 11/1985 | Gould et al. |
| 4,619,246 A | 10/1986 | Molgaard-Nielsen et al. |
| 4,748,982 A | 6/1988 | Horzewski et al. |
| 4,762,129 A | 8/1988 | Bonzel |
| 4,772,268 A | 9/1988 | Bates |
| 4,776,846 A | 10/1988 | Wells |
| 4,789,410 A | 12/1988 | Parizek |
| 4,921,479 A | 5/1990 | Grayzel |
| 4,923,413 A | 5/1990 | Michaels |
| 4,928,693 A | 5/1990 | Goodin et al. |
| 4,932,413 A | 6/1990 | Shockey et al. |
| 4,947,864 A | 8/1990 | Shockey et al. |
| 4,988,356 A | 1/1991 | Crittenden et al. |
| 5,024,234 A | 6/1991 | Leary et al. |
| 5,057,073 A | 10/1991 | Martin |
| 5,135,535 A | 8/1992 | Kramer |
| 5,163,921 A | 11/1992 | Feiring |
| 5,171,222 A | 12/1992 | Euteneuer et al. |
| 5,195,978 A | 3/1993 | Schiffer |
| 5,201,315 A | 4/1993 | Griffith |
| 5,203,338 A | 4/1993 | Jang |
| 5,205,822 A | 4/1993 | Johnson et al. |
| 5,234,407 A | 8/1993 | Teirstein et al. |
| 5,263,932 A | 11/1993 | Jang |
| 5,279,596 A | 1/1994 | Castaneda et al. |
| 5,290,232 A | 3/1994 | Johnson et al. |
| 5,314,408 A | 5/1994 | Salmon et al. |
| 5,324,269 A | 6/1994 | Miraki |
| 5,327,885 A | 7/1994 | Griffith |
| 5,336,184 A | 8/1994 | Teirstein |
| 5,342,297 A | 8/1994 | Jang |
| 5,389,087 A | 2/1995 | Miraki |
| 5,395,332 A | 3/1995 | Ressemann et al. |
| 5,395,335 A | 3/1995 | Jang |
| 5,400,789 A | 3/1995 | Griffith |
| 5,415,639 A | 5/1995 | VandenEinde et al. |
| 5,417,669 A | 5/1995 | Castaneda et al. |
| 5,458,584 A | 10/1995 | Ginn et al. |
| 5,462,530 A | 10/1995 | Jang |
| 5,496,346 A | 3/1996 | Horzewski et al. |
| 5,531,700 A | 7/1996 | Moore et al. |
| 5,540,236 A | 7/1996 | Ginn |
| 5,554,118 A | 9/1996 | Jang |
| 5,571,094 A | 11/1996 | Sirhan |
| 5,620,417 A | 4/1997 | Jang et al. |
| 5,626,600 A | 5/1997 | Horzewski et al. |
| 5,658,262 A | 8/1997 | Castaneda et al. |
| 5,735,828 A | 4/1998 | Jungnelius |
| 5,755,775 A | 5/1998 | Trerotola et al. |
| 5,800,414 A | 9/1998 | Cazal |
| 5,807,355 A | 9/1998 | Ramzipoor et al. |
| 5,814,064 A | 9/1998 | Daniel et al. |
| 5,817,100 A | 10/1998 | Igaki |
| 5,823,992 A | 10/1998 | Salmon et al. |
| 5,901,775 A | 5/1999 | Musschoot et al. |
| 5,910,154 A | 6/1999 | Tsugita et al. |
| 5,911,452 A | 6/1999 | Yan |
| 5,919,224 A | 7/1999 | Thompson et al. |
| 5,935,114 A | 8/1999 | Jang et al. |
| 5,947,925 A | 9/1999 | Ashiya et al. |
| 5,947,995 A | 9/1999 | Samuels |
| 5,948,191 A | 9/1999 | Solovay |
| 5,957,912 A | 9/1999 | Heitzmann |
| 5,997,523 A | 12/1999 | Jang |
| 6,001,118 A | 12/1999 | Daniel |
| 6,019,784 A | 2/2000 | Hines |
| 6,022,319 A | 2/2000 | Willard et al. |
| 6,053,932 A | 4/2000 | Daniel et al. |
| 6,056,719 A | 5/2000 | Mickley |
| 6,059,814 A | 5/2000 | Ladd |
| 6,066,100 A | 5/2000 | Willard et al. |
| 6,066,149 A | 5/2000 | Samson et al. |
| 6,068,610 A | 5/2000 | Ellis et al. |
| 6,096,009 A | 8/2000 | Windheuser et al. |
| 6,099,497 A | 8/2000 | Adams et al. |
| RE36,857 E | 9/2000 | Euteneuer et al. |
| 6,117,128 A | 9/2000 | Gregory |
| 6,123,715 A | 9/2000 | Amplatz |
| 6,129,739 A | 10/2000 | Khosravi |
| 6,142,973 A | 11/2000 | Carleton et al. |
| 6,142,987 A | 11/2000 | Tsugita |
| 6,159,195 A | 12/2000 | Ha et al. |
| 6,171,327 B1 | 1/2001 | Daniel et al. |
| 6,179,861 B1 | 1/2001 | Khosravi et al. |
| 6,196,995 B1 | 3/2001 | Fagan |
| 6,203,732 B1 | 3/2001 | Clubb et al. |
| 6,206,868 B1 | 3/2001 | Parodi |
| 6,210,500 B1 | 4/2001 | Zurfluh |
| 6,234,971 B1 | 5/2001 | Jang |
| 6,245,089 B1 | 6/2001 | Daniel et al. |
| 6,248,092 B1 | 6/2001 | Miraki et al. |
| 6,277,139 B1 | 8/2001 | Levinson et al. |
| 6,312,404 B1 | 11/2001 | Argo et al. |
| 6,312,407 B1 | 11/2001 | Zadno-Azizi et al. |
| 6,325,815 B1 | 12/2001 | Kusleika et al. |
| 6,336,934 B1 | 1/2002 | Gilson et al. |
| 6,346,093 B1 | 2/2002 | Allman et al. |
| 6,346,116 B1 | 2/2002 | Brooks et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,371,971 B1 | 4/2002 | Tsugita et al. |
| 6,383,171 B1 | 5/2002 | Gifford et al. |
| 6,383,196 B1 | 5/2002 | Leslie et al. |
| 6,391,044 B1 | 5/2002 | Yadav et al. |
| 6,425,909 B1 | 7/2002 | Dieck et al. |
| 6,450,987 B1 | 9/2002 | Kramer |
| 6,454,786 B1 | 9/2002 | Holm et al. |
| 6,458,099 B2 | 10/2002 | Dulta et al. |
| 6,461,370 B1 | 10/2002 | Gray et al. |
| 6,485,501 B1 | 11/2002 | Green |
| 6,494,907 B1 | 12/2002 | Bulver |
| 6,511,492 B1 | 1/2003 | Rosenbluth et al. |
| 6,520,978 B1 | 2/2003 | Blackedge et al. |
| 6,530,939 B1 | 3/2003 | Hopkins et al. |
| 6,537,294 B1 | 3/2003 | Boyle et al. |
| 6,537,295 B2 | 3/2003 | Peterson |
| 6,544,280 B1 | 4/2003 | Daniel et al. |
| 6,551,269 B2 | 4/2003 | Clemens et al. |

(56) References Cited

U.S. PATENT DOCUMENTS

| | | |
|---|---|---|
| 6,602,271 B2 | 8/2003 | Adams et al. |
| 6,613,013 B2 | 9/2003 | Haarala et al. |
| 6,632,241 B1 | 10/2003 | Hancock et al. |
| 6,652,505 B1 | 11/2003 | Tsugita |
| 6,656,203 B2 | 12/2003 | Roth et al. |
| 6,669,665 B2 | 12/2003 | Jayaraman |
| 6,740,061 B1 | 5/2004 | Oslund et al. |
| 6,773,448 B2 | 8/2004 | Kusleika et al. |
| 6,786,919 B1 | 9/2004 | Escano et al. |
| 6,929,652 B1 | 8/2005 | Andrews et al. |
| 6,969,396 B2 | 11/2005 | Kralik et al. |
| 6,979,343 B2 | 12/2005 | Russo et al. |
| 7,001,425 B2 | 2/2006 | McCuliagh et al. |
| 7,169,165 B2 | 1/2007 | Belef et al. |
| 7,955,351 B2 | 6/2011 | Von Lehe et al. |
| 9,456,889 B2 | 10/2016 | Von Lehe et al. |
| 2001/0025186 A1 | 9/2001 | Kramer |
| 2002/0004667 A1 | 1/2002 | Adams et al. |
| 2002/0022858 A1 | 2/2002 | Demond et al. |
| 2002/0042626 A1 | 4/2002 | Hanson et al. |
| 2002/0042627 A1 | 4/2002 | Brady et al. |
| 2002/0045916 A1 | 4/2002 | Gray et al. |
| 2002/0055747 A1 | 5/2002 | Cano et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0091409 A1 | 7/2002 | Sutton et al. |
| 2002/0095141 A1 | 7/2002 | Belef et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0128678 A1 | 9/2002 | Petersen |
| 2002/0128680 A1 | 9/2002 | Pavlovic |
| 2002/0133092 A1 | 9/2002 | Nawrocki et al. |
| 2002/0161392 A1 | 10/2002 | Dubrul |
| 2002/0161394 A1 | 10/2002 | Macoviak et al. |
| 2002/0165576 A1 | 11/2002 | Boyle |
| 2002/0165598 A1 | 11/2002 | Wahr et al. |
| 2002/0188314 A1 | 12/2002 | Anderson et al. |
| 2003/0004537 A1* | 1/2003 | Boyle ............... A61F 2/013 606/200 |
| 2003/0004541 A1 | 1/2003 | Linder et al. |
| 2003/0023264 A1 | 1/2003 | Dieck et al. |
| 2003/0032941 A1 | 2/2003 | Boyle et al. |
| 2003/0040771 A1 | 2/2003 | Hyodoh et al. |
| 2003/0078605 A1 | 4/2003 | Bashiri et al. |
| 2003/0100917 A1 | 5/2003 | Boyle et al. |
| 2003/0130684 A1 | 7/2003 | Brady et al. |
| 2003/0153942 A1 | 8/2003 | Wang et al. |
| 2003/0171770 A1 | 9/2003 | Kusleika et al. |
| 2003/0171771 A1 | 9/2003 | Anderson et al. |
| 2003/0176884 A1 | 9/2003 | Berrada et al. |
| 2003/0176887 A1 | 9/2003 | Petersen |
| 2003/0187474 A1 | 10/2003 | Keegan et al. |
| 2003/0187495 A1 | 10/2003 | Cully et al. |
| 2003/0233117 A1* | 12/2003 | Adams ............... A61F 2/013 606/200 |
| 2004/0153118 A1 | 8/2004 | Clubb et al. |
| 2004/0153119 A1 | 8/2004 | Kusleika et al. |
| 2004/0158277 A1 | 8/2004 | Lowe et al. |
| 2004/0215167 A1 | 10/2004 | Belson |
| 2004/0254602 A1 | 12/2004 | Von Lehe et al. |
| 2004/0260333 A1 | 12/2004 | Dubrul et al. |
| 2005/0113804 A1 | 5/2005 | Von Lehe et al. |
| 2005/0119686 A1 | 6/2005 | Clubb |
| 2005/0131449 A1 | 6/2005 | Salahieh et al. |
| 2005/0192620 A1 | 9/2005 | Cully et al. |
| 2006/0122643 A1 | 6/2006 | Wasicek et al. |
| 2006/0129181 A1 | 6/2006 | Callol et al. |
| 2007/0032815 A1* | 2/2007 | Devaux ............... A61F 2/01 606/200 |
| 2011/0230861 A1 | 9/2011 | Von Lehe et al. |

FOREIGN PATENT DOCUMENTS

| | | |
|---|---|---|
| EP | 0592720 A1 | 4/1994 |
| EP | 0592720 B1 | 4/1994 |
| EP | 0807448 A1 | 11/1997 |
| EP | 1181900 A2 | 2/2002 |
| EP | 1226795 A2 | 7/2002 |
| EP | 1351737 B1 | 7/2005 |
| WO | WO 9406372 A1 | 3/1994 |
| WO | WO 9425096 A1 | 11/1994 |
| WO | WO 9601591 A1 | 1/1996 |
| WO | WO 9725002 A1 | 7/1997 |
| WO | WO 9838920 A1 | 9/1998 |
| WO | WO 9839053 A1 | 4/1999 |
| WO | WO 9916382 A2 | 4/1999 |
| WO | WO 9934749 A1 | 7/1999 |
| WO | WO 0016705 A1 | 3/2000 |
| WO | WO 0049970 A1 | 8/2000 |
| WO | WO 0053119 A1 | 9/2000 |
| WO | WO 0053120 A1 | 9/2000 |
| WO | WO 0056245 A2 | 9/2000 |
| WO | WO 0058964 A1 | 10/2000 |
| WO | WO 0067669 A1 | 11/2000 |
| WO | WO 0067670 A1 | 11/2000 |
| WO | WO 0108595 A1 | 2/2001 |
| WO | WO 0108596 A1 | 2/2001 |
| WO | WO 0115629 A1 | 3/2001 |
| WO | WO 0121100 A1 | 3/2001 |
| WO | WO 0121246 A1 | 3/2001 |
| WO | WO 0135857 A1 | 5/2001 |
| WO | WO 0180776 A1 | 11/2001 |
| WO | WO 0189413 A2 | 11/2001 |
| WO | WO 0240090 A1 | 5/2002 |
| WO | WO 0243595 A2 | 6/2002 |
| WO | WO 02054988 A2 | 7/2002 |
| WO | WO 02062266 A2 | 8/2002 |
| WO | WO 02069846 A2 | 9/2002 |
| WO | WO 02094111 A2 | 11/2002 |
| WO | WO 03009781 A2 | 2/2003 |
| WO | WO 03015859 A2 | 2/2003 |
| WO | WO 03105721 A2 | 12/2003 |
| WO | WO 2006089178 | 8/2006 |

OTHER PUBLICATIONS

US 6,461,371 B1, 10/2002, Mcinnes (withdrawn)
Search Report and Written Opinion for International Application No. PCT/US2004/002587, dated Jul. 30, 2005, 8 pp.
Search Report and Written Opinion for International Application No. PCT/US2004/002756, dated Jul. 30, 2005, 3 pp.
Search Report and Written Opinion for International Application No. PCT/US2004/002757, dated Jul. 30, 2005, 4 pp.
Search Report and Written Opinion and International Preliminary Report on Patentability for Counterpart International Application No. PCT/US2006/005762, dated Aug. 18, 2007, 17 pp.
Examination Report from counterpart European Application No. 11193811.4, dated Mar. 10, 2016, 3 pp.
Extended European Search Report from counterpart European Application No. 11193811.4, dated Nov. 28, 2012, 7 pp.
European Search Report from counterpart European Application No. 11193811.4, dated Jan. 4, 2013.
Communication pursuant to Article 94(3) EPC from counterpart European Application No. 06735425.8, dated Jun. 4, 2010, 3 pp.
Response to the Examination Report dated Jun. 4, 2010, from counterpart European Application No. 06735425.8, filed on Dec. 13, 2010, 16 pp.
Prosecution History from U.S. Appl. No. 11/357,404, dated from Mar. 29, 2010 through Feb. 2, 2011, 41 pp.
Prosecution History from U.S. Appl. No. 13/149,464, dated from Apr. 15, 2013 through Jun. 15, 2016, 139 pp.

* cited by examiner

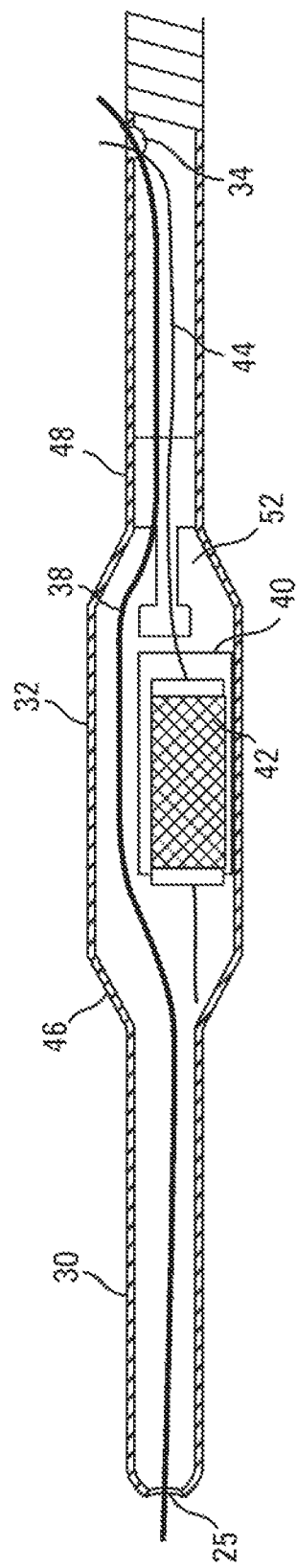

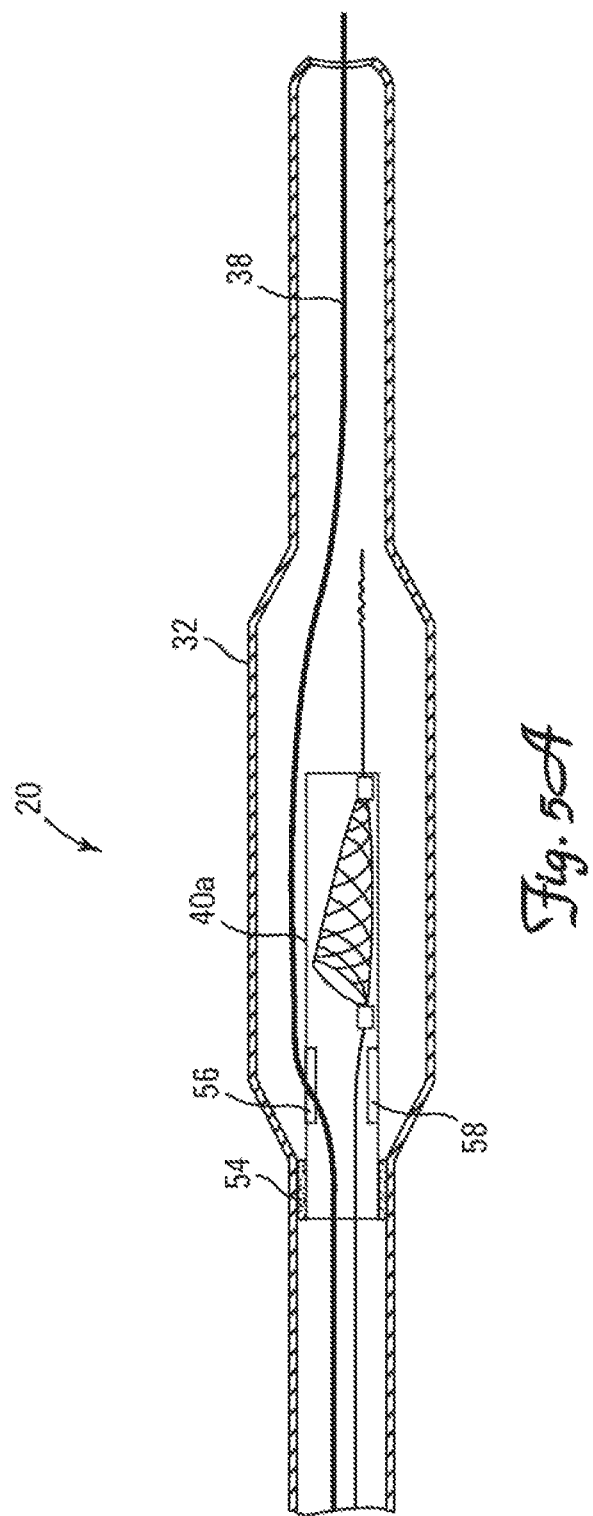

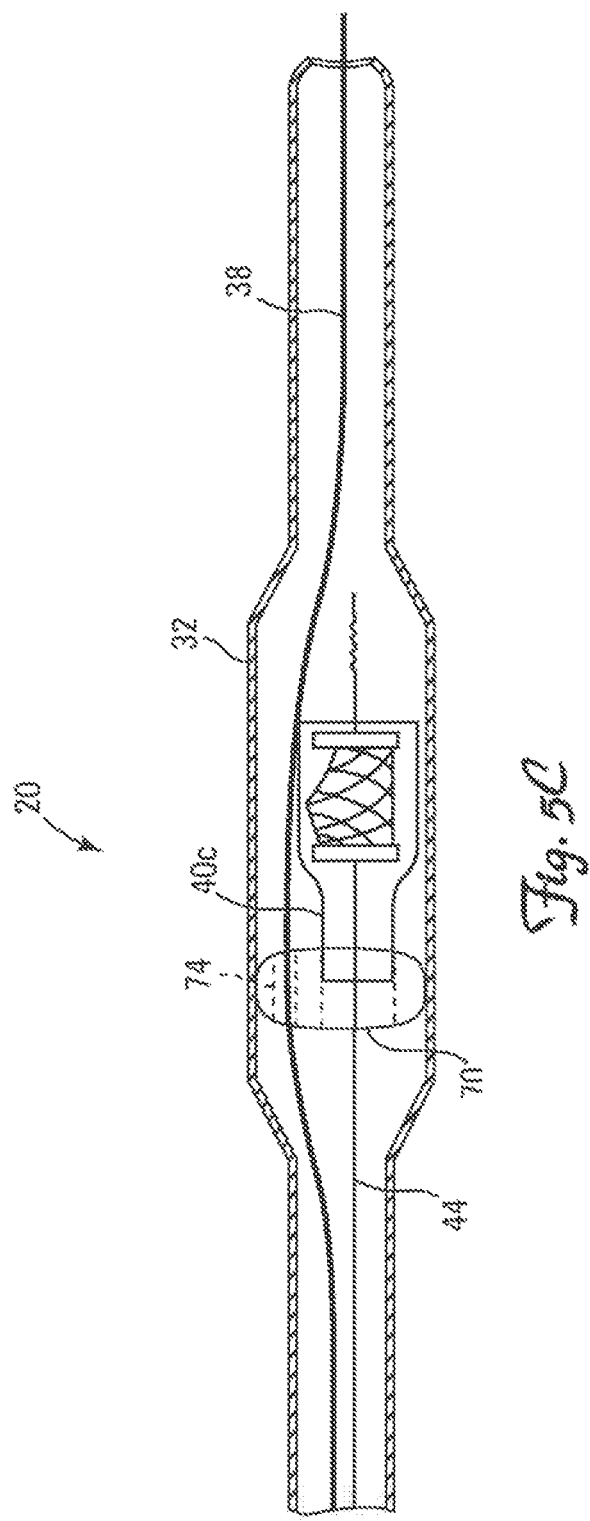

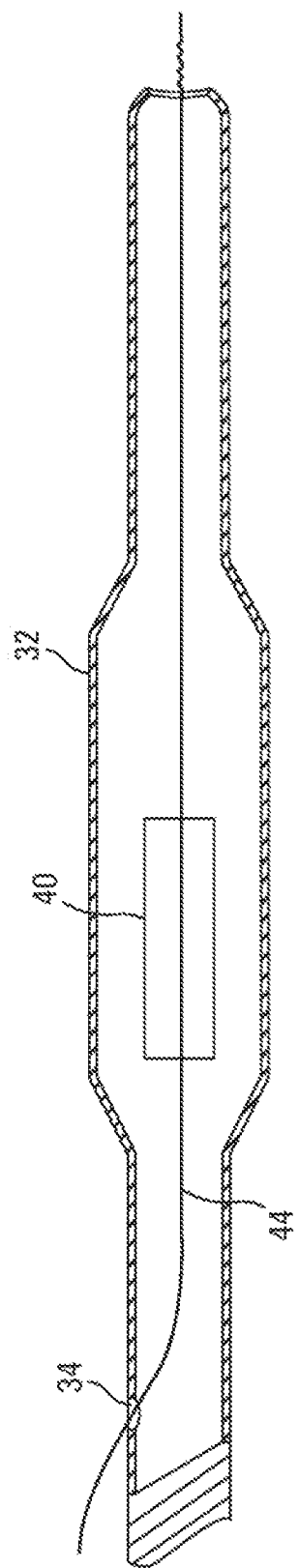

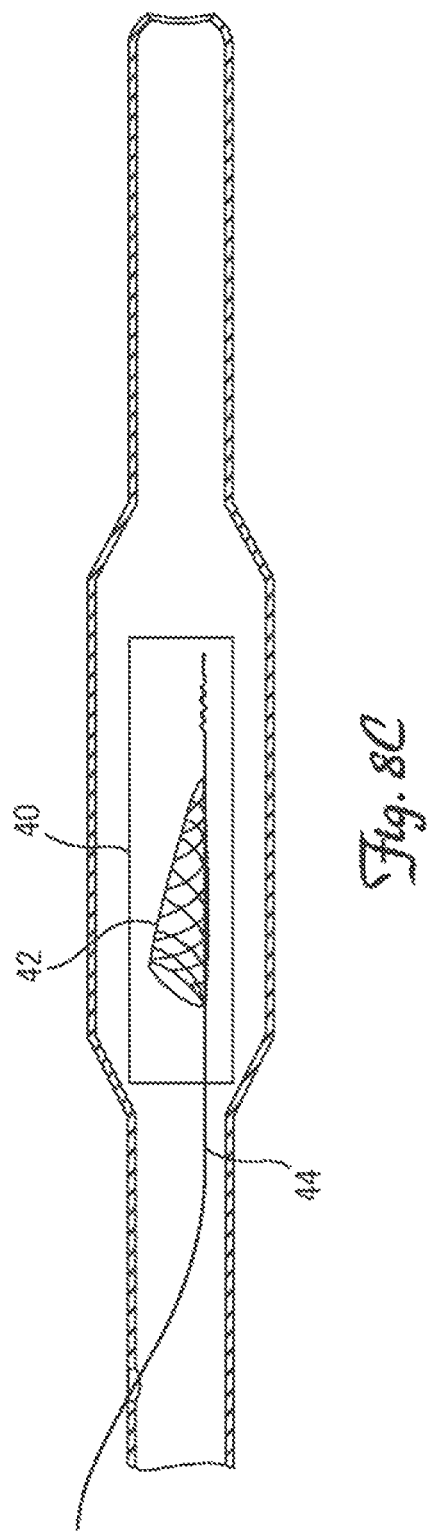

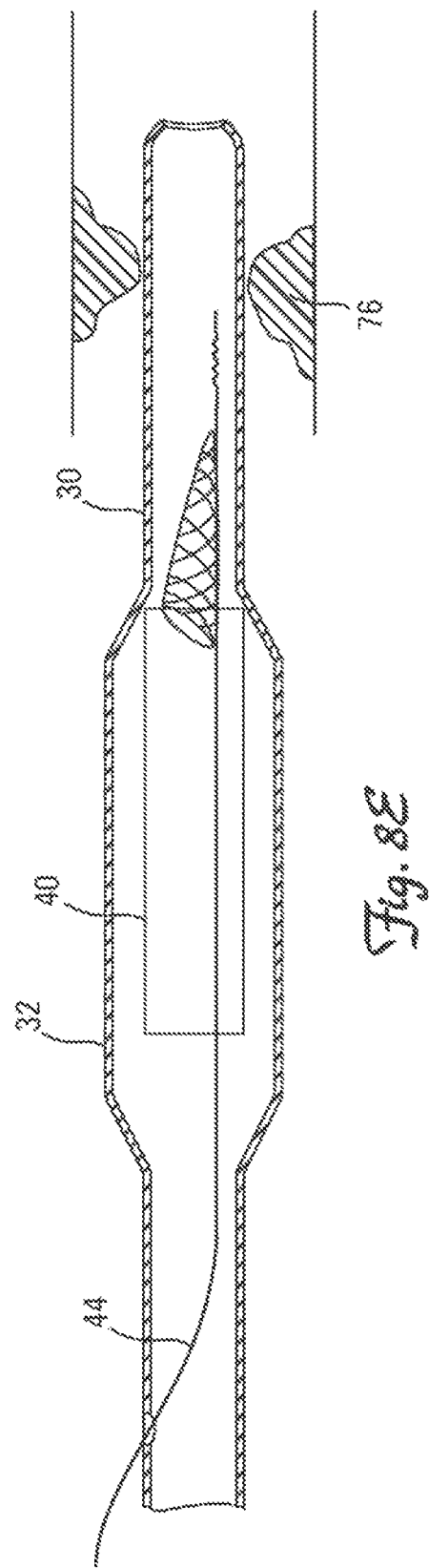

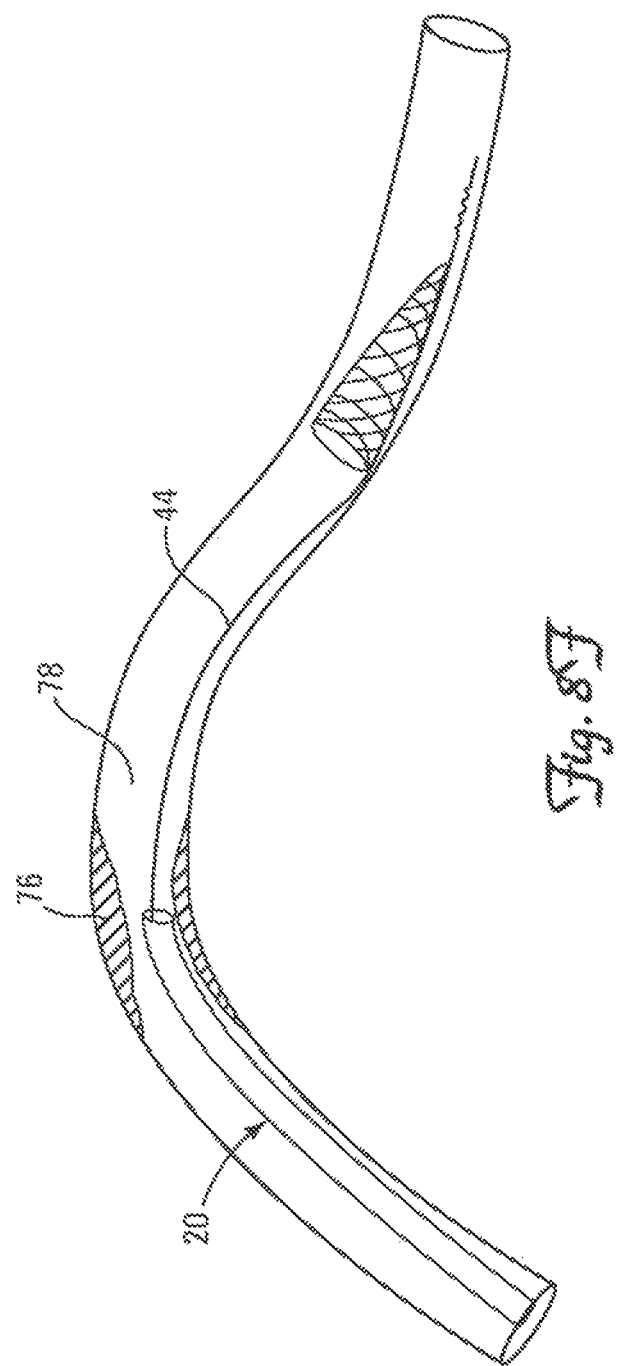

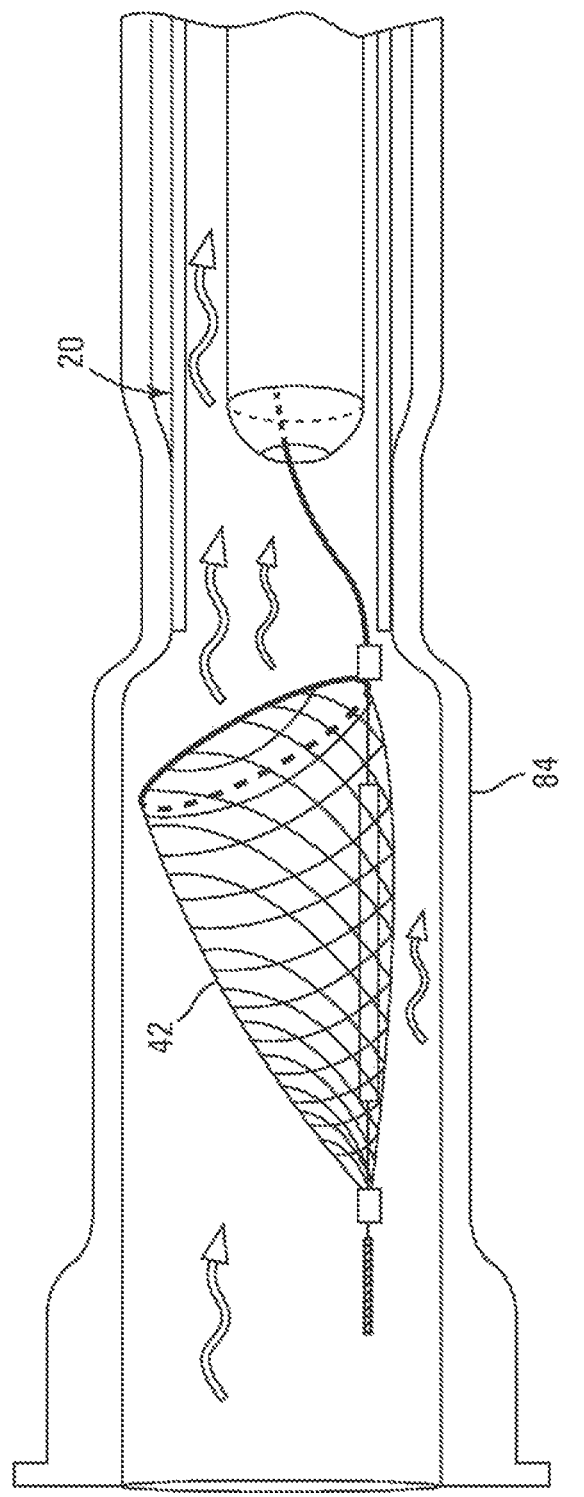

RAPID EXCHANGE CATHETERS AND EMBOLIC PROTECTION DEVICES

This application is a continuation of U.S. application Ser. No. 13/149,464, filed May 31, 2011, now U.S. Pat. No. 9,456,889, which is a continuation of U.S. application Ser. No. 11/357,404, filed Feb. 17, 2006, now U.S. Pat. No. 7,955,351, which claims the benefit of U.S. Provisional Application No. 60/654,389, filed Feb. 18, 2005, the contents of each of which are hereby incorporated by reference herein.

FIELD OF THE INVENTION

This invention relates to devices used in a blood vessel or other lumen in a patient's body, in particular, the present invention relates to rapid exchange catheters and embolic protection devices that may be delivered thereby.

BACKGROUND OF THE INVENTION

Coronary vessels, partially occluded by plaque, may become totally occluded by thrombus or blood clot causing myocardial infarction, angina, and other conditions. Carotid, renal, peripheral, and other blood vessels can also be restrictive, to blood flow and require treatment. A number of medical procedures have been developed to allow for the removal or displacement (dilation) of plaque or thrombus from vessel walls to open a channel to restore blood flow and minimize the risk of myocardial infarction. For example, atherectomy or thrombectomy devices can be used to remove atheroma or thrombus. In cases where infusion of drugs or aspiration of thrombus may be desired, infusion or aspiration catheters can be placed near the treatment site to infuse or aspirate. In cases where the treatment device can be reasonably expected to shed emboli, embolic protection devices can be placed near the treatment site to capture and remove emboli. In other cases, a stent is placed at the treatment site. Both embolic protection devices and stents can be placed in or near the treatment site using delivery catheters.

In percutaneous transluminal coronary angioplasty (PICA), a guidewire guide catheter are inserted into the femoral artery of a patient near the groin, advanced through the artery, over the aortic arch, and into a coronary artery. An inflatable balloon is then advanced into the coronary artery, across a stenosis or blockage, and the balloon inflated to dilate the blockage and open a flow channel through the partially blocked vessel region. One or more stents may also be placed across the dilated region or regions to structurally maintain the open vessel. Balloon expandable stents are crimped onto a balloon in the deflated state and delivered to the lesion site. Balloon expansion expands the stem against the lesion and arterial wall. Alternatively, self-expanding stents can be restrained in a sheath, delivered to the treatment site, and the sheath removed to allow expansion of the stem.

Embolic protection devices have been developed to prevent the downstream travel of materials such as thrombi, grunions, emboli, and plaque fragments. Devices include occlusive devices and filters. Occlusive devices, for example distal inflatable balloon devices, can totally block fluid flow through the vessel. The material trapped by the inflatable devices can remain in place until removal using a method such as aspiration. However, aspiration cannot remove large particles because they will not fit through the aspiration lumen. Also, aspiration is a weak acting force and will not remove a particle unless the tip of the aspirating catheter is very close to the particle to be removed. During the occlusion, the lack of fluid flow can be deleterious. In coronary applications, the lack of perfusing blood flow can cause angina. In carotids, seizure can result from transient blockage of blood flow, in both coronaries and carotids, it is not possible to predict who will suffer from angina or seizure due to vessel occlusion. If a procedure starts with an occlusive device, it may be necessary to remove it and start over with a filter device.

Occlusive embolic protection devices can also be placed proximal to the treatment site. Debris generated at or near the treatment site will not be transported from the treatment site if a proximal occlusive device substantially stops blood flow through the vessel. The material generated during treatment can remain in place until removal using a method such as aspiration. Generally, proximal occlusive embolic protection devices suffer from many of the same limitations as distal occlusive embolic protection devices.

Other catholic protection devices are filters. Filters can allow perfusing blood flow during the emboli capture process. The filters can advance downstream of a site to be treated and expand to increase the filter area. The filter can capture emboli, such as grumous or atheroma fragments, until the procedure is complete or the filter is occluded. When the filter reaches its capacity, the filter may then be retracted and replaced.

Embolic protection devices can be delivered over wires and within guide catheters. The embolic protection methods are normally practiced ancillary to another medical procedure, for example PTCA with stenting or atherectomy. The embolic protection procedure typically protects downstream regions from emboli resulting from practicing the therapeutic interventional procedure. In the example of PTCA, the treating physician must advance a guidewire through the aorta, over the aortic arch, and into a coronary ostium. Advancing the guidewire through tortuous vessels from a femoral artery approach can be difficult and vary with both the patient and the vessel site to be treated. Guide wires are typically selected by the treating physician, based on facts specific to the patient and therapeutic situation, and also on the training, experience, and preferences of the physician. In particular, a physician may have become very efficient in using a specific guidewire to access the left coronary ostium and then advance a balloon catheter over the positioned guidewire. The efficacy of the procedure may depend on the physician being able to use a favored guidewire.

In the example PTCA procedure, a guide catheter extends proximally from the patient's groin area, and may be about 100 centimeters long. A 320 centimeter guidewire is placed into the guide catheter and extended distal of the guide into a coronary vessel, leaving about a 200 centimeter long guidewire proximal region extending from the guide catheter. The embolic protection device delivery catheter, nominally about 130 centimeters in length, can advance over the guidewire and within the guide catheter, until a length of guidewire extends from both the guide catheter and delivery catheter. The guidewire can then be retracted and removed from the patient. In some methods, the embolic protection device then advances through and out of the positioned delivery catheter, to the target site to be protected or filtered. In other methods, delivery is accomplished by disposing the embolic protection filter device within the delivery catheter distal region, and advancing the delivery catheter and embolic protection device together within the guide catheter, optionally over the guidewire, and deploying the filter by retracting the delivery catheter while maintaining the position of the filter, thus forcing the filter distally out of the delivery catheter.

Advancement of the delivery catheter over a single length, nominally 170 centimeter long guidewire presents a problem. The treating physician can only advance the filter delivery catheter about 40 centimeters over the guidewire until the delivery catheter advances into the patient and the guidewire is inaccessible within the delivery catheter. The guidewire position should be controlled at all times so as to not be dislodged by the advancing delivery catheter from the hard acquired guidewire position within the patient.

One solution to this problem is to use a guidewire at least double the length of the delivery catheter as described above. A 320 centimeter long guidewire can extend at least about 150 centimeters from the patient's groin, having an accessible region exposed at all phases of delivery catheter placement. However, the length of the 320 centimeter guidewire makes manipulating and rotating the guidewire very difficult for the treating physician, Additional personnel can hold the extra length of the guidewire to prevent the added wire length front falling to the floor, where it would become contaminated. However, not all cardiac catheter laboratories have personnel available to maintain control of the long guidewire. In many labs, the physician is working alone in the sterile field. Advancing a device delivery catheter over a positioned, favored, and short (175 centimeter) guidewire would be inherently more efficacious than requiring use of an unfamiliar, disfavored, or double length guidewire to position the delivery catheter.

Another alternative catheter design is the monorail or rapid exchange type such as that disclosed in U.S. Pat. No. 4,762,129, issued Aug. 9, 1988, to Bonzel. This catheter design utilizes a conventional inflation lumen plus a relatively short parallel guiding or through lumen located at its distal end and passing through the dilatation balloon. Guide wires used with PTCA balloon catheters are typically 175 centimeters in length and are much easier to keep within the sterile operating field than 300 to 340 centimeter guidewires. This design enables the short externally accessible rapid exchange guidewire lumen to be threaded over the proximal end of a pre-positioned guidewire without the need for long guidewires.

Still needed in the art are improved designs for rapid exchange delivery catheters. Such delivery catheters can be used to deliver various treatment and/or diagnostic devices including embolic protection devices.

It is desirable to place a distal protection device at a chosen location in order to achieve good seating between the device and the wall of the vessel. Frequently it is necessary to match the protection device diameter with the vessel diameter, and vessels are known to taper or to have diameters that vary due to disease. It is also desirable to place the protection device in a relatively disease free portion of the vessel so as to minimize liberation of emboli from the wall of the vessel due to interaction with the protection device. Further, it is desirable that the device remains at the desired location during the procedure. Excessive motion of the wire or elongate guide member used to deliver the device can advance a protection device distally, beyond branch vessels, which thereby become unprotected from emboli.

Distal protection devices typically are mounted on a wire or tube that functions as a guidewire. As used herein the term guidewire means either a traditional guidewire or other elongate member or hollow tube that is used in delivering the distal protection device. The protection device can be either a filter or an occlusive device such as a balloon. The distal protection devices are either fixedly attached to the guidewire or attached so as to permit a limited amount of motion between the device and the guidewire. Frequently, the same guidewire used to carry the devices used to guide various catheters to and from the treatment site. For example, during the procedure, catheters may be exchanged over this guidewire. When catheters are exchanged inadvertent wire movement can cause the protection device to move within the vessel. Excessive wire motion can also retract a protection device proximally, where it can potentially become entangled in a stem or even be inadvertently removed from the vessel being protected. In some vessels, when guide catheters are repositioned, the protection device also tends to move within the vessel. This is undesirable because captured emboli can be released and/or new emboli can be formed distal to the protection device, blood vessels can be damaged, and/or the device can entangle with an implant such as a stent. Therefore, it is clear that too much movement of the device within the vessel could have catastrophic results.

Some work already has been done to provide for limiting the movement of a distal protection device or distal filer with respect to a guidewire. For example, a guidewire having a distal stop is described in WO 01/35857 (Tsugita et al.). The filter slides on the guidewire hut cannot slide off the wire due to the distal stop. Another device which includes a slideable vascular filter having both distal and proximal sliding elements that move independently of each other over a mandrel is described in WO 01/21100 (Kusleika et al). While this system meets many of the needs in the art, it limits the range of motion of the filtration device on the guidewire, and the precision with which it can be placed is limited. Still further embodiments of devices which allow increased independence of movement of the guidewire without moving the embolic protection device are disclosed in U.S. Pat. No. 6,773,448 B2, issued Aug. 10, 2004, to Kusleika et al.

Another known limitation of distal protection devices relates to win bias. It is well known that a guidewire will conform to the outside vessel on advancement of the wire in a distal direction and will conform to the interior of a curved vessel during retraction of the wire. Most distal protection devices are attached to wires, and when they are deployed in vessel curvature the wire bias will alternately move the device between the inside and the outside of the vessel curve. For filters this can defeat the protection effect by compressing the filter opening. For occlusion devices the wire bias effect can cause excessive motion of the occlusion device with potential liberation of embolic debris from the vicinity of the occlusive element.

Some work already has been done to provide for limiting the radial movement of a guidewire relative to a distal protection device. For example, a protection device having a proximal loop is described in U.S. Pat. No. 6,740,061 B1, issued May 25, 2004, to Oslund et al.), the contents of which are incorporated herein by reference. A loop is provided proximal to the filter to immobilize the wire against the vessel wall regardless of wire bias. While this system meets many of the needs in the art, it adds bulk to the device and thereby limits crossing profile.

It would be desirable to have a distal protection system that can be precisely placed at a location within the vasculature and that can accommodate some range of axial and/or radial wire motion without disturbing the device's position. Further, when the embolic protection device is a filter it would be desirable that the host wire which carries the filter be centered within the lumen when the device is deployed.

SUMMARY OF THE INVENTION

The present invention provides a rapid exchange catheter which can be used to deliver various vascular treatment and/or diagnostic devices. The invention also provides an improved embolic protection device which can be delivered, for example, by the rapid exchange catheter disclosed herein.

The invention provides a catheter comprising: an elongated member configured to be advanced along a vascular path of a patient, the elongated member having a proximal portion, a distal portion, a proximal end, a distal end, a housing portion adjacent to and proximal of the distal portion, and a sidewall exit port proximal of the housing section; the distal end comprising a distal port; the distal portion comprising an indwelling medical device delivery structure; the housing portion defining an interior cavity and the housing portion comprising a housing member having an interior space dimensioned for housing an indwelling medical device; the elongated member comprising a lumen extending at least from the exit port to the distal port, the housing member being disposed within the lumen, and the lumen being dimensioned in the housing portion to receive a guidewire outside of the interior space of the housing member.

The invention further provides a method for positioning a medical device within a patient's blood vessel, the method comprising: providing a catheter described herein and advancing the medical device to a target site within the patient's blood vessel.

The invention provides a method for positioning a catheter within a patient's blood vessel, the method comprising: providing a catheter described herein; providing a guidewire having a proximal end and a distal end; advancing the guidewire to a larger site within the patient's blood vessel; and advancing the catheter over the guide wire by inserting the guidewire through the lumen between the distal port and the sidewall exit port.

The invention further provides a distal tip of a host wire of an embolic protection device comprising: a wire comprising a first constant diameter region having a first diameter, a second constant diameter region baying a second diameter, and a third constant diameter region having a third diameter, the second constant diameter region having a smaller diameter than the first constant diameter region, and the third constant diameter region having a smaller diameter than the second constant diameter region; a first tapering transition region between the first constant diameter region and the second constant diameter region; and a second tapering transition region between the second constant diameter region and the third constant diameter region.

The invention provides a medical device for maintaining an embolic protection device in a blood vessel in a patient's body comprising: an elongate support member, an elongate side branch member connected to the elongate support member; and an embolic protection device attached to the elongate side branch member by a proximal embolic protection device slider, the elongate side branch member being adapted to maintain the embolic protection, device centered in the vessel.

The invention further provides a medical device for filtering emboli from blood flowing in a blood vessel of patient comprising: an elongate support member; an elongate side branch member connected to the elongate support member; and a filter element being expandable from a collapsed configuration when the filter element is restrained to an expanded configuration when the filter element is unrestrained, wherein the filter element comprises a material having pores, wherein the filter element has proximal and distal portions, the filter element having a shape in the expanded configuration which defines an interior cavity having a proximal facing opening, the filter element being attached to the elongate side branch member by a proximal filter element slider, the elongate side branch member being adapted to maintain the filter element centered in the vessel.

BRIEF DESCRIPTION OF THE DRAWINGS

FIGS. 3A and 38 are cross-sectional views of a portion of the delivery end of the catheter of FIG. 1 according to a first embodiment of the invention.

FIGS. 5A, 5B and 5C are cross-sectional views of a portion of the delivery end of the catheter of FIG. 1 according to further embodiments of the invention.

FIGS. 8A to 8F disclose steps in the method of loading and using a delivery catheter in accordance with be present invention.

FIGS. 10A and 10B disclose use of a removable packaging sheath to flush the catheter of the present invention prior to use.

DETAILED DESCRIPTION OF THE PREFERRED EMBODIMENTS

Figure 1:
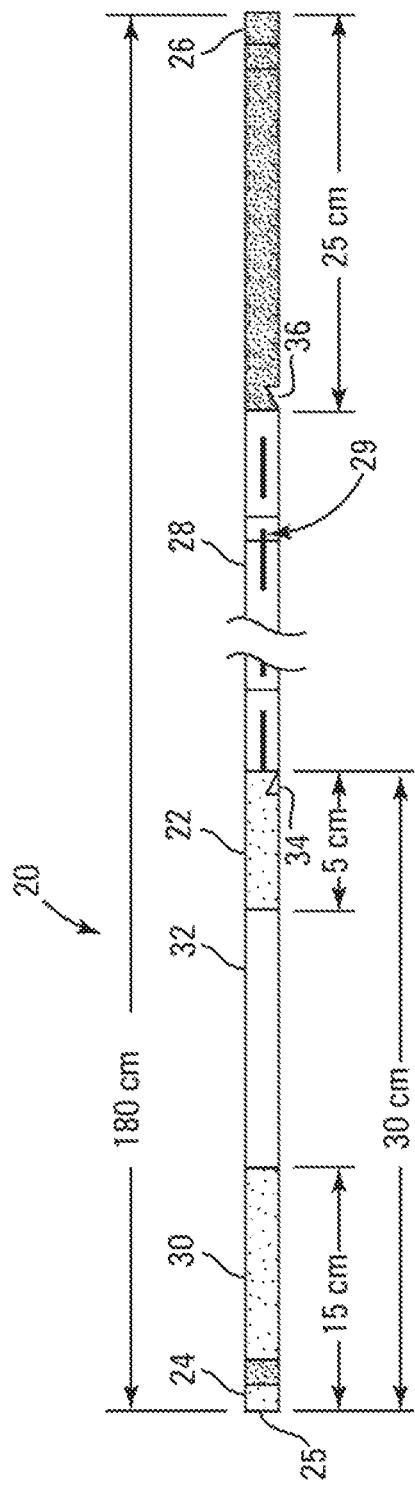
FIG. 1 shows a double-ended catheter having features that are examples of inventive aspects in accordance with the principles of the present disclosure.

The terms "distal" and "proximal" as used herein refer to the relative position of the guidewire and catheters in a lumen. The most "proximal" point of the catheter is the end of the catheter extending outside the body closest to the physician. The most "distal" point of the catheter is the end of the catheter placed farthest into a body lumen from the entrance site. The same meaning is applied to these terms when used in describing an embolic protection device.

The use of the phrases "distal embolic protection device" or "embolic protection device" herein refers to embolic protection devices that are occlusive, diverting, and/or filtering. The term "embolic protection device" is meant to include devices used to protect a target site and located either proximal to, at, or distal to the treatment site.

The invention provides a catheter comprising an elongated member configured to be advanced along a vascular path of a patient, the elongated member having a proximal portion, a distal portion, a proximal end, a distal end, a housing portion adjacent to and proximal of the distal portion, and a sidewall exit port proximal of the housing section; the distal end comprising a distal port; the distal portion comprising an indwelling medical device delivery structure; the housing portion defining an interior cavity and the housing portion comprising a housing member having an interior space dimensioned for housing an indwelling medical device; the elongated member comprising a lumen extending at least from the exit port to the distal port, the housing member being disposed within the lumen, and the lumen being dimensioned in the housing portion to receive a guidewire outside of the interior space of the housing member. In one embodiment, the housing member is secured at a fixed location within the housing portion. In another embodiment, the housing portion comprises distal and proximal housing sections and the housing member can move axially within the housing portion. In another embodiment, the housing member can move axially between the proximal and distal sections of the housing portion.

In one embodiment, the housing portion and distal portion have outer diameters and the outer diameter of the housing portion is larger than the outer diameter of the distal portion. In another embodiment, the housing portion and distal portion have inner diameters and the inner diameter of the housing portion is larger than the inner diameter of the distal portion. In another embodiment, the housing portion and distal portion have outer diameters and the outer diameter of the housing portion is larger than the outer diameter of the distal portion, and the housing portion and distal portion have inner diameters and the inner diameter of the housing portion is larger than the inner diameter of the distal portion.

In one embodiment, the proximal housing section comprises a stop member. The stop member may be tubular. The stop member may comprise one or more sidewall slots that allow additional pathways for the guidewire.

In one embodiment, the elongated member has an inner wall defining the lumen and the housing member is adjacent to the inner wall. In another embodiment, the housing member is centered within the lumen.

In one embodiment, the housing, portion comprises distal and proximal housing sections and the proximal housing section comprises the housing comprise one or more sidewall slots that allow additional pathways for a guidewire.

In one embodiment, wherein the elongated member has an inner wall defining the lumen, and the housing member is suspended within the housing portion by a grommet that is affixed to the inner wall. In an embodiment, the grommet has an outer periphery, and the entire outer periphery of the grommet contacts the inner wall. The housing member may be centered within the lumen. The grommet may comprise one OT more openings which allow passage of the guidewire. In one embodiment, the grommet comprises a single opening that allows passage of the guidewire, and in another embodiment the grommet comprises two openings that allow passage of the guidewire.

The housing member may be tubular. The catheter may comprise a ramp in the lumen that causes a guidewire to be directed out the exit port. In one embodiment, at least a portion of the housing portion is transparent.

The proximal portion of the catheter may comprise an indwelling medical device retrieval structure. The proximal portion may comprise a sidewall port. The proximal end of the catheter may comprise a rolled tip. The proximal end of the catheter may comprise a shapeable tip.

In one embodiment, the distal port has a diameter and the distal end comprises a removable delivery tip transition component that reduces the diameter of the distal port. The removable delivery tip transition component may comprise a tearable spirally wrapped material and a string that extends along the side of the delivery catheter.

The invention provides an assembly comprising a guidewire and a catheter described herein. The invention provides an assembly comprising a medical device and a catheter described herein. The assembly may further comprise a guidewire. The medical device can be selected from an embolic protection device, balloon catheter, stent delivery catheter, atrial appendage occlusion device, mitral valve remodeling device, or septal defect closure device. In one embodiment, the medical device is an embolic protection device. In one embodiment the embolic protection device is a filter, and in another embodiment, embolic protection device is an occlusive device. In one embodiment, the medical device is adapted to be delivered and retrieved by the elongated member.

The invention provides an assembly comprising a catheter described herein and a removable packaging sheath having an end adapted to accommodate a fluid filled syringe for flushing the catheter.

The invention provides a method for positioning a medical device within a patient's blood vessel, the method comprising: providing a catheter described herein; and advancing the medical device to a target site within the patient's blood vessel.

The invention provides a method for positioning a catheter within a patient's blood vessel, the method comprising: providing a catheter described herein; providing a guidewire having a proximal end and a distal end; advancing the guidewire to a target site within the patient's blond vessel; and advancing the catheter over the guide wire by inserting the guidewire through the lumen between the distal port and the sidewall exit port. In one embodiment, the embolic protection device is leaded into the catheter prior to advancing the catheter over the guide wire. In an embodiment, the catheter is advanced over the guide wire to a treatment site, the guide wire is removed, and the embolic protection device is advanced out of the catheter.

The invention provides a distal tip of a host wire of an embolic protection device comprising: a wire comprising a first constant diameter region having a first diameter, a second constant diameter region having a second diameter, and a third constant diameter region having a third diameter, the second constant diameter region having a smaller diameter than the first constant diameter region, and the third constant diameter region having a smaller diameter than the second constant diameter region; a first tapering transition region between the first constant diameter region and the second constant diameter region; and a second tapering transition region between the second constant diameter region and the third constant diameter region.

The invention provides a medical device for maintaining an embolic protection device in a blood vessel in a patient's body comprising: an elongate support member; an elongate side branch member connected to the elongate support member; and an embolic protection device attached to the elongate side branch member by a proximal embolic protection device slider, the elongate side branch member being adapted to maintain the embolic protection device centered in the vessel. In one embodiment, the elongate side branch member is adapted to maintain the elongate support member centered in the lumen. In another embodiment, the embolic protection device is attached to the elongate support member. The embolic protection device may be a filter or an occlusive device.

The invention provides a medical device for filtering emboli from blood flowing in a blood vessel of patient comprising: an elongate support member; an gate side branch member connected to the elongate support member; and a filter element being expandable from a collapsed configuration when the filter element is restrained to an expanded configuration when the filter element is unrestrained, wherein the filter element comprises a material having pores, wherein the filler element has proximal and distal portions, the filter element having a shape in the expanded configuration which defines an interior cavity having a proximal facing opening, the filter element being attached to the elongate side branch member by a proximal filter element slider, the clot side branch member being adapted to maintain the filter element centered in the vessel. In one embodiment, the elongate side branch member is adapted to maintain the elongate support member centered in the lumen. In another embodiment, the material having pores is self-expanding. In another embodiment, the material having pores comprises wires braided to form pores.

In one embodiment, the elongate support member has distal and proximal portions and the filter element is attached, to the elongate support member in a distal portion of the elongate support member. In another embodiment, the elongate support member has a distal end and the filter element attached to the elongate support member at or near the distal end.

In one embodiment, the elongate side branch member is connected to the elongate support member by a proximal side branch member slider and a distal side branch member slider. In another embodiment, the filter element is attached to the elongate support member by a distal filter element slider. In one embodiment, when the medical device is in its expanded configuration, (i) the proximal side branch member slider is proximal of the proximal filter element slider, (ii) the proximal filter element slider is proximal of the distal side branch member slider, and (iii) the distal side branch member slider is proximal of the distal filter element slider. In one embodiment, the elongate support member includes a proximal stop and a distal stop with both stops being distal to the distal side branch member slider and proximal of the distal filter element slider.

In one embodiment, the elongate side branch member is connected to the elongate support member by a proximal side branch member slider. In an embodiment, the elongate side branch member has a distal end that comprises a distal end stop and the distal end is not connected to the elongate support member. In one embodiment, the fitter element is attached to the elongate support member by a distal filter element slider. In an embodiment, when the medical device is in its expanded configuration, the proximal side branch member slider is proximal of the proximal filter element slider. In one embodiment, the elongate member includes an elongate member stop, the elongate member stop being distal of the proximal side branch member slider and being proximal of the distal filter element slider.

In one embodiment, the elongate support member has a distal end portion and the elongate side branch member is a loop portion of the elongate support member at the distal end portion. In an embodiment, the proximal filter element slider provides the only connection between the filter element and the elongate side branch member, and the filter element is not connected to the elongate support member.

In one embodiment, the filter element is attached to the elongate side branch member by the proximal filter element slider and a distal filter element slider. In an embodiment, the elongate support member has a distal end, a tube is fixed on the elongate side branch member between the proximal and distal filter element sliders, and the tube slideably receives the distal end of the elongate support member.

In one embodiment, the elongate support member comprises a slot in which a sliding element is disposed and the elongate side branch member is connected to the elongate support member by the proximal sliding element. In an embodiment, a distal dual side branch member and filter element slider connects the elongate side branch member and the filter element to the elongate support member.

In one embodiment be elongate side branch member is connected to the elongate support member by a proximal side branch member slider and a distal dual side branch member and filter element slider, the distal dual side branch member and filter element slider connecting the filter element to the elongate support member. In an embodiment, the elongate member includes a stop distal to the proximal side branch member slider and proximal of the distal dual side branch member and filter element slider.

A. Rapid Exchange Delivery Catheter

In the drawing figures included herein the rapid exchange delivery catheter is shown as comprising one end of a double ended catheter. The other end of the catheter is used for recovering a medical device from a lumen. A similar catheter is disclosed in U.S. Patent Application Publication No. 2004/0254602 A1, published Dec. 16, 2004, to Lehe at al., the contents of which are incorporated herein by reference. However, the concepts disclosed herein are equally applicable to single ended rapid exchange catheters.

Specifically, this invention applies to any catheter used in conjunction with a guidewire or elongate support member for delivery. The concept is universal. Embolic protection device delivery catheters, balloon catheters, and stent delivery catheters with or without a balloon are typical catheters to which the invention can be applied. The concept can also be applied to percutaneous delivery and recovery catheters for atrial appendage occlusion devices, mitral valve remodeling devices, septal defect closure devices, and the like.

The components of the catheters of the invention are made from biocompatible materials such as metals or polymeric materials. If necessary, these metals or polymeric materials can be treated to impart biocompatibility by various surface treatments, as known in the art. Suitable materials include stainless steel, titanium and its alloys, cobalt-chromium-nickel-molybdenum-iron alloy (commercially available under the trade designation ELGILOY™), carbon fiber and its composites, and polymers such as liquid crystal polymers, polyetheretherketone (PEEK), polyimide, polyester, high density polyethylene, PEBAX®, various nylons, and the like. A shape memory or superelastic material such as nitinol or shape memory polymer is also suitable. The size, thickness, and composition of materials are selected far their ability to perform as desired as well as their biocompatibility. It is to be understood that these design elements are known to one of skill in the art.

The material comprising the catheter is preferably at least partially radiopaque. This material can be made radiopaque by plating, or by using core wires, tracer wires, or fillers that have good X-ray absorption characteristics compared to the human body. Marker bands comprised of generally tubular radiopaque metals may be attached to the catheter.

The tip of the catheter may be a generally softer material so as to help prevent damage to a vessel wall as the tip is advanced through the vasculature. Softer materials such as PEBAX®, nylon, rubbers, urethane, silicone, ethylene vinyl acetate, and the like may be attached to the catheter by adhesives, overmolding, heat bonding, solvent bonding, and other techniques known in the art. The tip may have a geometry designed to assist with advancement of the catheter past intraluminal obstructions, such as any of those constructions contained within U.S. Pat. No. 6,979,343 B2, issued Dec. 27, 2005, to Russo et al., the contents of which are incorporated by reference herein.

The catheter is generally referred to as an embolic protection delivery/recovery catheter however it is contemplated that the embodiments of the catheters described herein may be used solely for delivery, solely for recovery, or for both delivery and recovery.

FIG. 1 shows a rapid exchange catheter 20 in accordance with the present invention. The catheter includes an elongated body 22 having first and second opposite end portions 24 and 26. The elongated body 22 is preferably sufficiently flexible to allow the device to be advanced through a curving vascular pathway without kinking and without puncturing the vessel wall. The first and second end portions 24 and 26 are both capable of leading the elongated member 22 through the vasculature depending upon the direction the elongated member 22 is inserted into the vasculature. The first and second end portions 24 and 26 are adapted for providing different functions. First end portion 24 is adapted for deploying an indwelling medical device such as a stent, graft or embolic protection device while the second end portion 26 is adapted for retrieving an indwelling medical device such as a stem graft or embolic protection device. As stated previously the present invention is directed to end portion 24 comprising the rapid exchange delivery portion of the catheter. The concepts disclosed herein are equally applicable to single ended rapid exchange delivery catheters. Additionally, although certain dimensions are stated with respect to the disclosed embodiments those dimensions are merely for purposes of illustration and other dimensions, as known by those of skill in the art, are within the scope of the present invention.

Catheter 22 includes a wire reinforced midsection 28. This section may be reinforced with a core wire 29 to enhance the pushability of the catheter. The core wire may be 0.014 inch (0.036 cm) in diameter.

In the context of the present invention catheter 20 will be described in terms of the use of the rapid exchange delivery catheter side. Therefore, unless otherwise stated, end portion 24 is referred to as the distal end. End portion 24 includes distal port 25. The catheter includes a distal portion 30 which may be approximately 15 centimeters in length. Distal portion 30 has a low crossing profile which is adapted to allow that portion of the catheter to cross a lesion in the vasculature. For example, distal portion 30 may have an outer diameter of approximately 0.042 inch (0.11 cm). Just proximal of distal portion 30 is a housing portion 32. Housing portion 32 has a slightly increased ID and OD as compared to distal portion 30 for the purpose of providing a housing section for a medical device such as an embolic protection device which will be described in more detail hereafter. Elongate member 22 includes an exit port 34 which is spaced proximally of housing section 32. For example, exit port 34 may be spaced 5 centimeters from housing portion 32 and 30 centimeters from end portion 24. Exit port 34 is sized to allow passage of both a primary guidewire and a host wire that carries an embolic protection device. Elongate member 22 includes a second exit port 36 for use in connection with the recovery side of catheter 20. Housing portion 32 may be at least semitransparent to ensure appropriate loading of the embolic protection device or other medical device both during packaging and even during use of the device by a physician.

Figure 2:
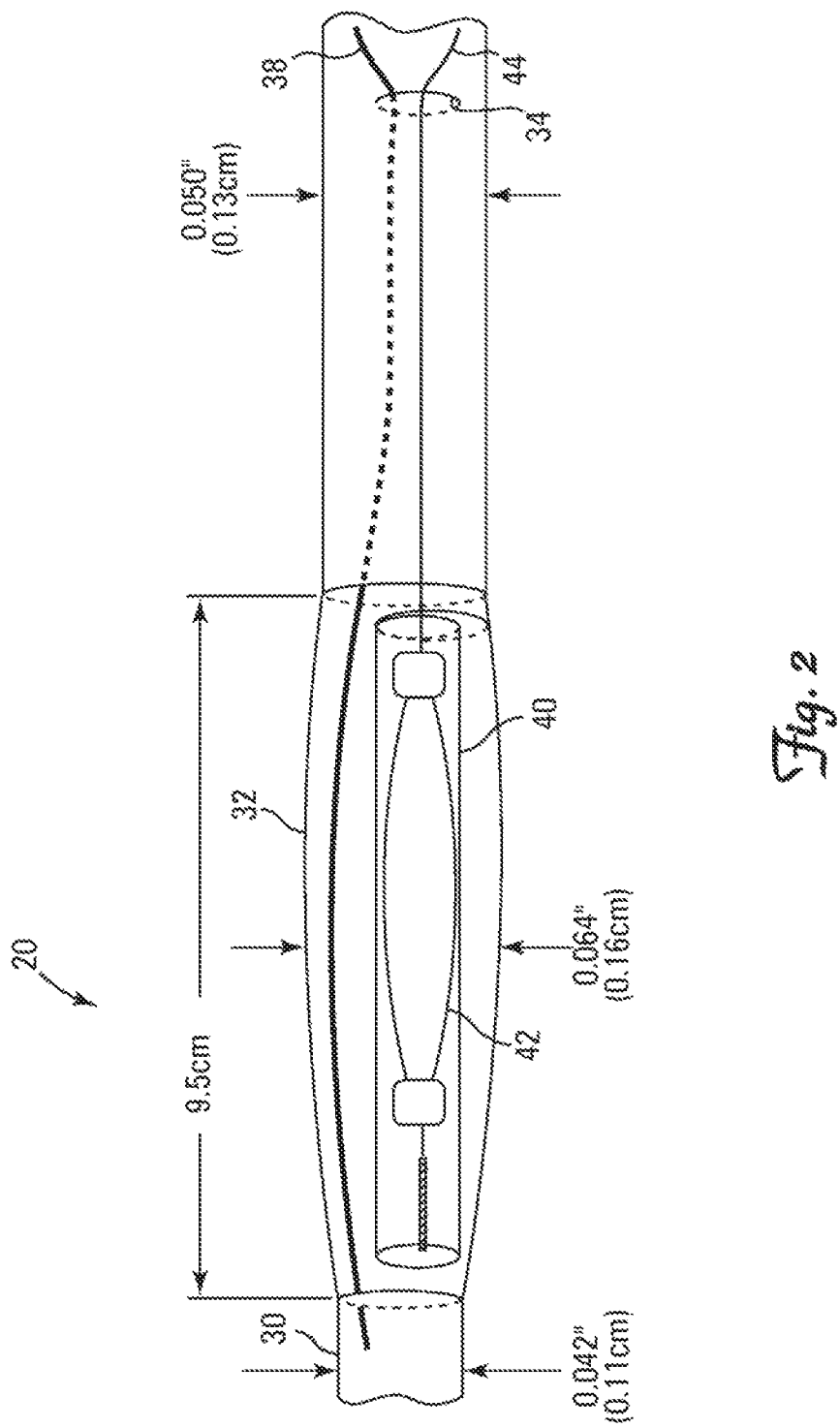
FIG. 2 is a schematic view of a portion of the delivery end of the double-ended catheter of FIG. 1.

FIG. 2 is another view of catheter 20 showing housing portion 32, a portion of distal portion 30 and exit port 34. In this figure the primary guidewire 38 has been loaded into the lumen of catheter 20 and exits through exit port 34. Within housing section 32 is a housing member 40 into which has been loaded an embolic protection device 42 carried by a support wire or host wire 44. Housing member 40 is shown as comprising a tubular shaped structure. However, other shapes are contemplated within the scope of the invention. Housing member 40 defines an interior cavity or space for containing the embolic protection device in its collapsed or delivery configuration. The exterior dimensions of housing member 40 are selected such that sufficient space is left within housing section 32 to allow for passage of the primary guidewire. Host wire 44 also exits the catheter lumen through exit port 34. Housing member 40 can be secured at a fixed location within housing section 32 as described in connection with FIGS. 5 to 7. Alternatively, housing member 40 may comprise a shuttle component which can move axially within housing section 32 between distal and proximal ends of the housing section as described in connection with FIGS. 3 and 4.

Figure 3A:
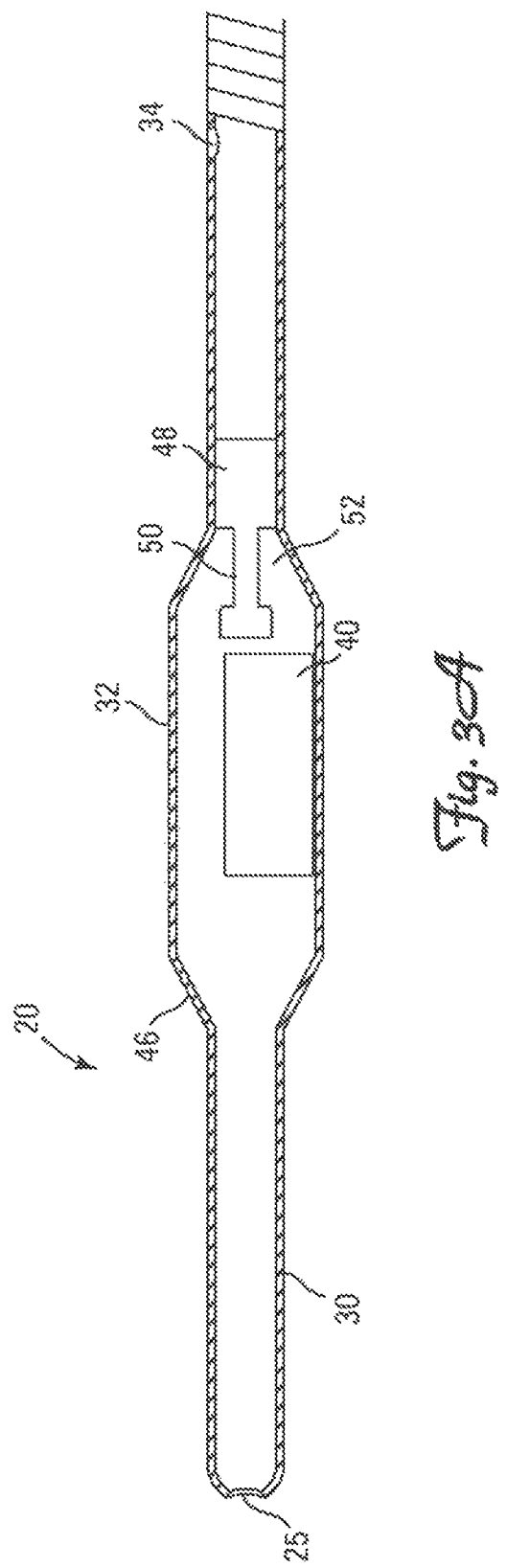
Figure 4:
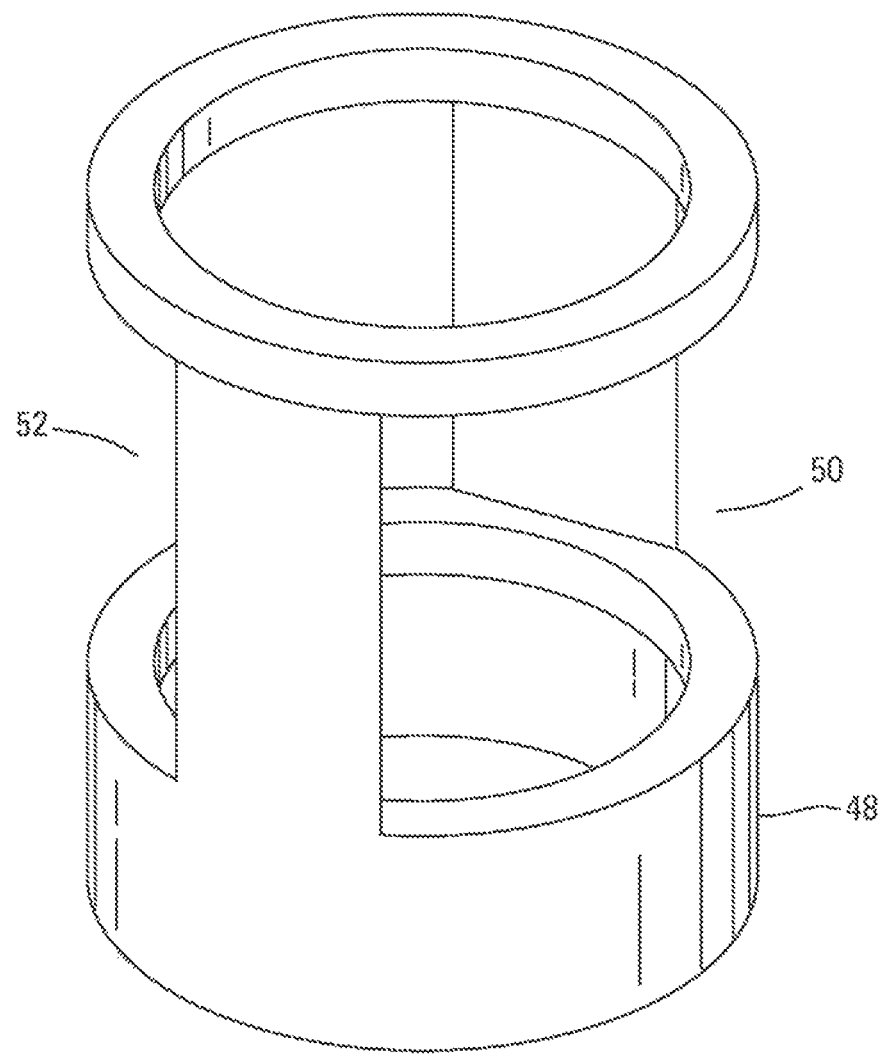
FIG. 4 is a perspective view of a stop member shown in FIGS. 3A and 3B.

FIG. 3A discloses an embodiment wherein housing member 40 is configured to move axially within housing section 32 between a reduced diameter end 46 of housing section 32 and a stop member 48 which is attached or bonded within the lumen of catheter 20 at the proximal end of housing section 32. Stop member 48 is provided with one or more openings or slots 50 and 52. Stop member 48 is shown in more detail in FIG. 4. The stop member is sized and configured to ensure that housing member 40 will not wedge into the proximal transition between the larger diameter housing section 32 and the adjacent smaller diameter proximal portion of the catheter. If the housing member were to wedge into this proximal transition section the primary guidewire would be prevented from passing around the shuttle thereby blocking its access to the proximal section of the catheter and exit port 34. Stop member 48 functions to space housing member 40 distally of the proximal end of housing section 32. Slots 50 and 52 are sized to ensure that the primary guidewire is able to pass through the slots into the proximal section of the catheter to access the exit port. FIG. 3B shows the embodiment of FIG. 3A where both the primary guidewire 38 and the embolic protection device 42 have been loaded into the delivery catheter. The primary guidewire 38 passes through the exit port 34 and distal port 25.

Figure 5B:
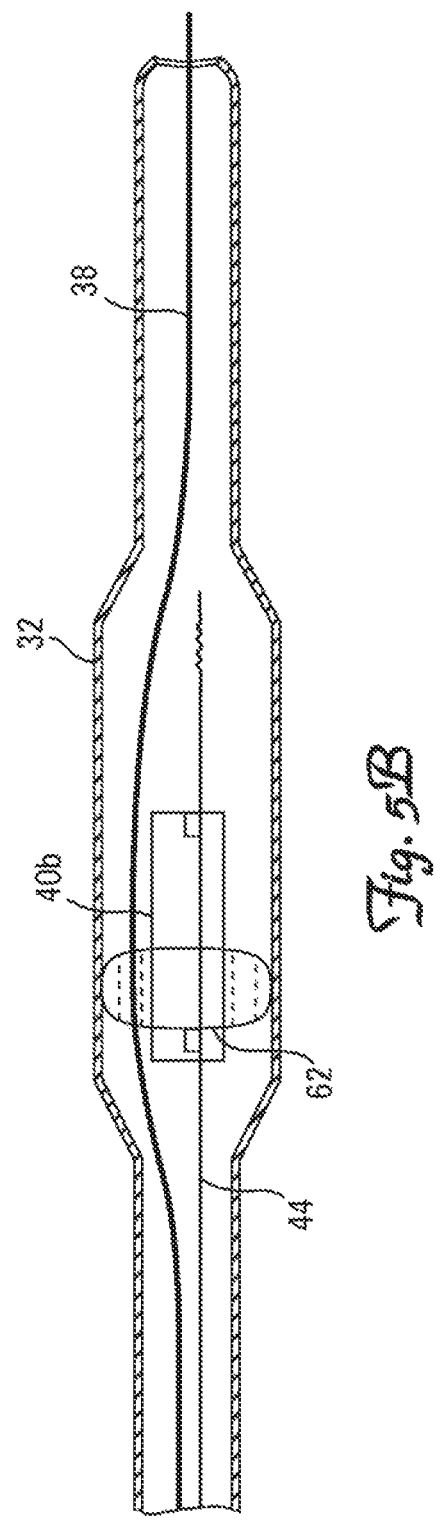

FIGS. 5A, 5B and 5C disclose alternative embodiments of the catheter where housing member 40 is secured at a fixed location within housing section 32. Each of these embodiments incorporates a mechanism to freeze the housing member or shuttle within housing section 32. The mechanism may be in the form of a support structure that will suspend the housing or shuttle inside of the housing section. This prevents movement of the housing within the catheter hut will still allow loading of the embolic protection device, passage of the primary guidewire around the shuttle into the proximal end of the catheter and out the exit port. The mechanism for suspension of the housing is designed to allow adequate clearance both distally and proximally to ensure space for the primary guidewire to pass. The suspension structure is also configured to low the wire to pass around the housing. The suspension mechanism may retain the housing to one side of the catheter lumen. The suspension mechanism may be, for example, a clasp, rib-like structure, washer-like structure, or other material embedded into the wall of the catheter lumen. The suspension piece can be constructed of the catheter material itself or can be an independent piece either wedged or adhered to the catheter inner wall.

Figure 6A:
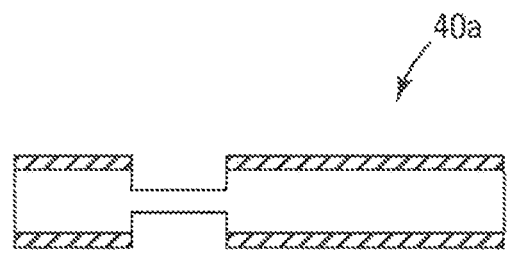
FIGS. 6A and 6B are alternate embodiments of a housing member shown in FIG. 5A.
Figure 6B:
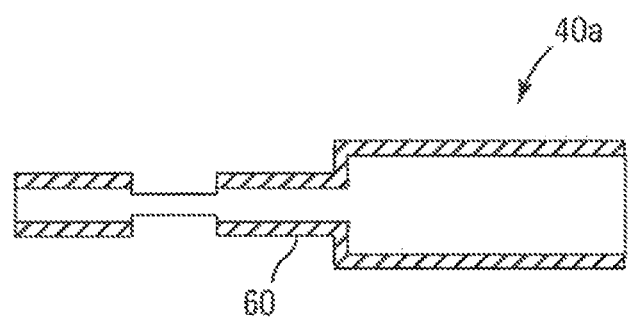

In the embodiment shown in FIG. 5A a housing member 40a has a proximal portion 54 winch is affixed or bonded to the inner wall of catheter 20 at the proximal end of housing section 32. Housing member 40a is provided with one or more slots 56 and 58 which are sized to allow passage of the primary guidewire from the distal end of the catheter out exit port 34 (not shown). Housing member 40a is sized to allow sufficient space between housing member 40a and the inner wall of housing section 32 so that the primary guidewire can be passed. FIG. 6A is a cross-sectional view of housing member 40a disclosed in FIG. 5A. FIG. 6B is a cross-sectional view of an alternative configuration of housing member 40a which includes a reduced diameter section 60 which creates a step which acts as a stop when positioning the embolic protection device within housing member 40a.

Figure 7A:
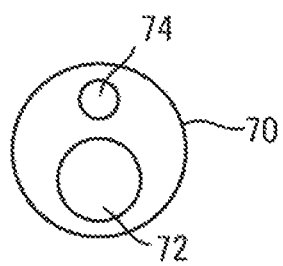
FIGS. 7A and 7B are views of a grommet utilized in the embodiments of FIGS. 5C and 5B respectively.
Figure 7B:
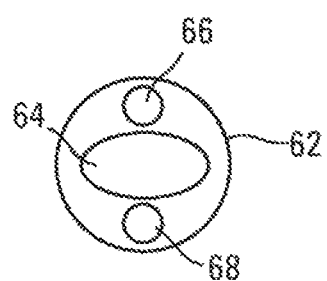

In the embodiments of FIGS. 5B and 5C the housing member is suspended within housing section 32 by use of a grommet which is sized to have an outer periphery which can be affixed to the inner wall of the catheter in the housing section. In FIG. 58 a grommet 62 comprises a multi-lumen extrusion which can be heat bonded to the catheter lumen. As shown in FIG. 7B grommet 62 comprises an opening 64 to receive housing member 40b and one or more openings 66 and 68 that allow passage of the primary guidewire.

In the embodiment of FIG. 5C a dual lumen extruded grommet 70 is provided. As shown in FIG. 7A grommet 70 comprises a dual lumen extrusion having a first opening 72 to receive housing member 40c and a second opening 74 to allow passage of the primary guidewire. In this embodiment housing member 400 is positioned to one side of the housing section 32 allowing adequate clearance for passage of the primary guidewire. In this embodiment housing member 40c includes a reduced diameter portion to act as a stop for the embolic protection device. The grommets could alternatively be fabricated with metal or rubber components.

FIGS. 8A to 8F show in simplified form the steps of loading and using the rapid exchange delivery catheter of the present invention. These steps are generally applicable to all of the embodiments disclosed herein including those embodiments where the housing member is configured to move or float within the housing section and those embodiments where the housing member is suspended or fixed at a particular location within the housing section.

Figure 8A:
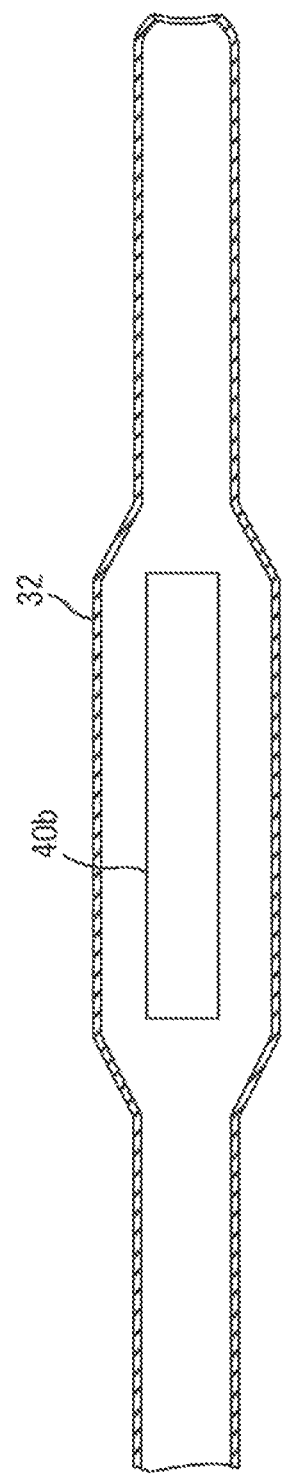
Figure 8D:
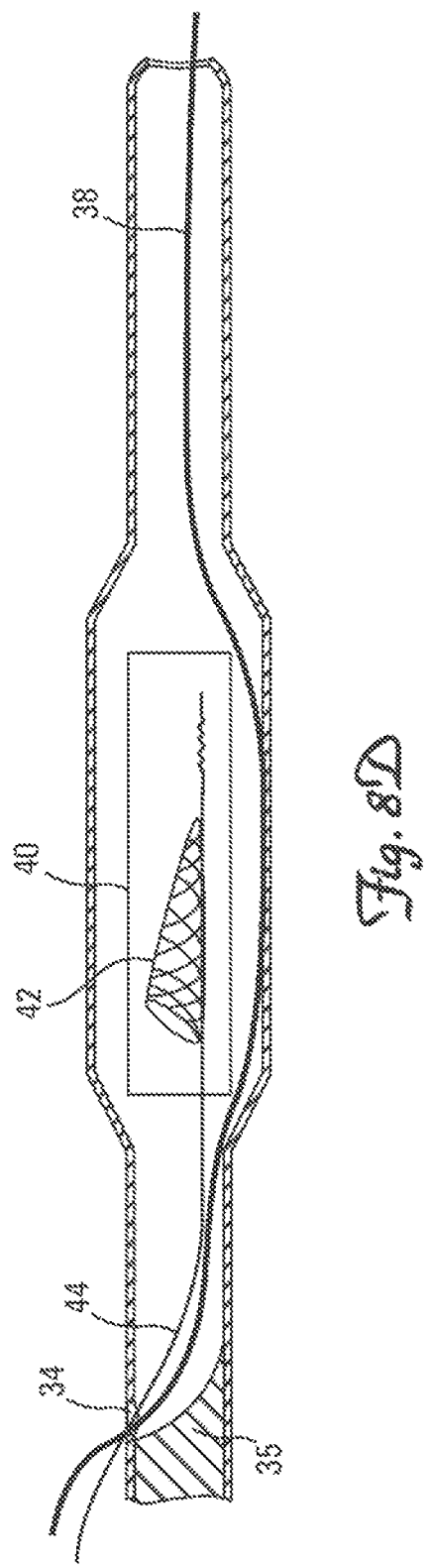

FIG. 8A shows a distal portion of the catheter prior to loading of either an embolic protection device or the primary guidewire. In FIG. 8B the host wire 44 has been inserted through the lumen of the catheter, through housing member 40 and out exit port 34. This depicts a partially preloaded configuration of the embolic protection device within the catheter. The catheter and embolic protection device may be packaged within this partially preloaded configuration. In FIG. 8C the embolic protection device has been withdrawn proximally so that it is contained within housing member 40. In FIG. 8D the catheter and filter have been loaded over the primary guidewire 38. The distal end of the guidewire is hack loaded through the distal end of the catheter. Since the embolic protection device takes up the entire lumen of housing member 40 the guidewire is directed around housing member 40 as the catheter is moved over the guidewire. The lumen of the proximal delivery portion of the catheter may end at exit port 34. The catheter may be provided with an optional ramp 35 or other structure which causes the distal end of the guidewire to be directed out exit port 34 as the catheter is moved over the guidewire.

Once the guidewire has been loaded over the guidewire it may be advanced through the vasculature to a treatment location as shown in FIG. 8E. The treatment location may comprise a lesion 76 which is crossed by the distal portion 30 of the catheter. In FIG. 8E the primary guidewire has been removed. The filter is deployed out of the distal end of the catheter by urging the host wire distally. Once the embolic protection device is deployed the delivery catheter is removed. The host wire can then be used as a guidewire for an interventional treatment device of choice such as a balloon catheter and/or a stent delivery catheter. In FIG. 8F an embolic protection device in the form of a filter is shown deployed at a location distal to lesion 76. A stent 78 has been deployed at the lesion. The recovery end of the catheter 20 is shown advanced over the host wire 44. The recovery end of the catheter preferably has a shapeable tip which can be angled or bent to facilitate tracking the recovery catheter through the deployed stent. The shapeable tip may be made of any of the materials that are described herein as being suitable components of the catheters. In particular, the shapeable tip may be heat-treated to be made more ductile, and may be made of a shape memory or super elastic alloy. Once the distal end of the recovery catheter has passed through the stent the embolic protection device can be withdrawn proximally into the lumen of the recovery catheter. The embolic protection device and recovery catheter are then withdrawn together from the vessel.

Figure 9A:
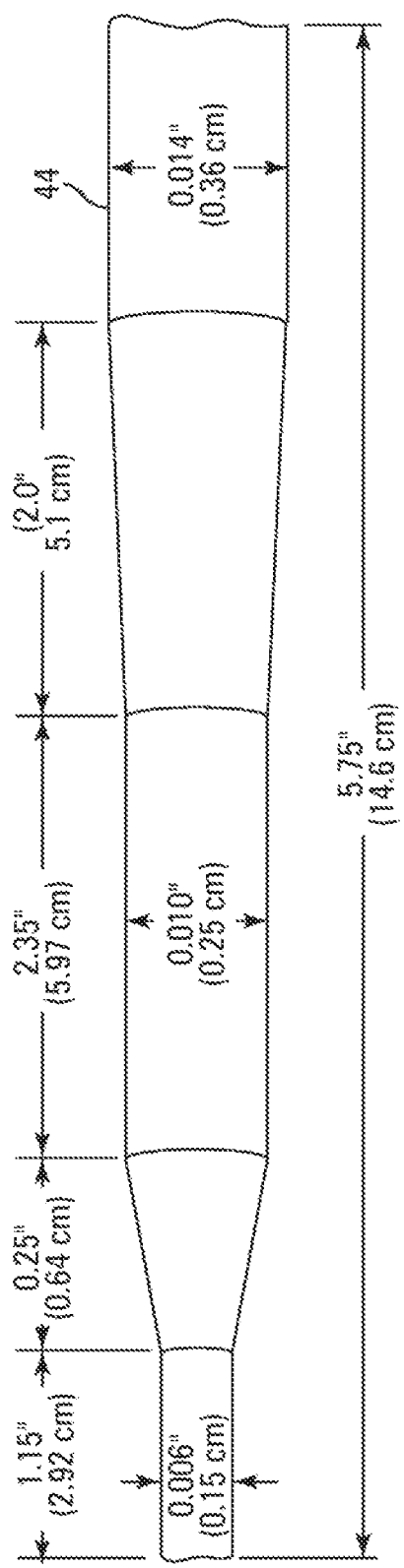
FIGS. 9A and 9B disclose features of the distal tip of a support wire and delivery catheter, respectively, in accordance with the present invention.
Figure 9B:
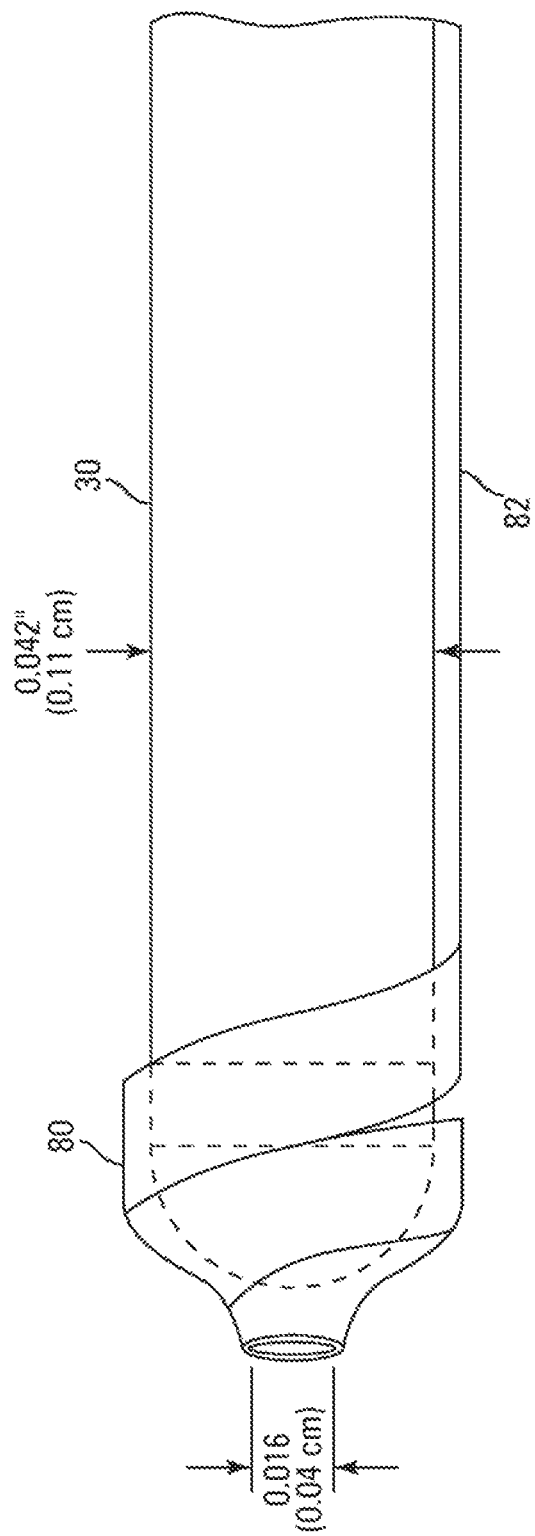

FIGS. 9A and 9B show additional features or configurations of the invention. FIG. 9A shows an alternative distal tip which can be incorporated into the design of host wire 44. Host wire 44 may include a configuration which tapers in a stepped manner from a diameter of 0.014 inch (0.036 cm) to 0.010 inch (0.025 cm) and then finally to 0.006 inch (0.015 cm). This stepped taper feature allows for more support and pushability of host wire 44 during delivery of the embolic protection device. As shown in FIG. 9A, the transition region from a diameter of 0.014 inch (0.036 cm) to 0.010 inch (0.025 cm) may have a length of 2.0 inches (5.1 cm). The 0.010 inch (0.025 cm) diameter region may have a length of 2.35 inches (5.97 cm). The transition region from a diameter of 0.010 inch (0.025 cm) to 0.006 inch (0.015 cm) may have a length of 0.25 inch (0.64 cm).

FIG. 9B shows a delivery tip transition component which can be used at the distal tip of the delivery catheter. Delivery tip transition component 80 is an optional component which may be used for the purpose of reducing the opening at the distal tip of the delivery catheter to a size which is more compatible with the size of the primary guidewire. For example, the primary guidewire may have a diameter of 0.014 inch (0.036 cm). Thus, in the embodiment disclosed in FIG. 9B the transition component 80 has a distal opening of 0.016 inch (0.041 cm). This allows the catheter to track over the guidewire with a tighter fit providing more fed fix the user. Transition component 80 may comprise a tearable spirally wrapped material which includes a string 82 which extends outside of the patient along side the delivery catheter. Once the delivery catheter is positioned the transition component can be removed by pulling string 82 in a proximal direction. This provides additional clearance for deployment of the embolic protection device from the distal end of the delivery catheter.

Figure 10B:
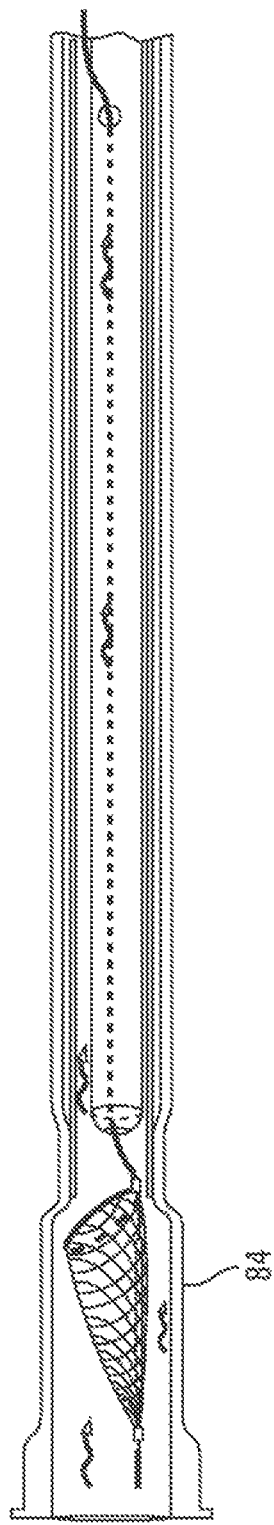

Another feature of the device is shown in FIGS. 10A and 10B. Specifically, the catheter may be packaged with a removable packaging sheath 84. Packaging sheath 84 has an end that is adapted to accommodate a fluid filled syringe (not shown). The syringe may be used to flush the embolic protection device 42 and catheter 20 when they are prepared for use. FIGS. 10A and 10B show fluid being flushed from the distal end to the proximal end of the delivery catheter 20.

B. Embolic Filter with Centered Wire

The invention encompasses the use of any filtration device to be deployed in a lumen or vessel of a patient. Although the examples relate generally to filter protection devices deployed distal to a treatment site, the device can also be deployed proximal to a treatment site in connection with interrupting or reversing flow through the vessel. In the case of a proximally deployed device, it will be advantageous to construct the device on a hollow elongate member so as to preserve access to the treatment site through the hollow member.

In a preferred embodiment, the distal protection system comprises a catheter that is loaded with an elongate support member or guidewire about which is disposed a distal protection filter. The elongate support member is structurally similar to a traditional guidewire in some respects. However, it is not used as a means at navigating the patient's vascular system and, therefore, does not need to be provided with all of the features of flexibility and steerability as does a traditional guidewire. With these differences in mind, the terms elongate support member and guidewire may be used interchangeably herein. A floppy tip (described further below) may be at the distal end of the elongate support member or guidewire. Typically, the filter is introduced into a blood vessel through an introducing catheter.

Methods of introducing guidewires and catheters and the methods for the removal of such devices from vessels are well known in the art of endovascular procedures. In a typical procedure using the device of this invention, the elongate support member and filter are loaded into an introducing sheath or catheter and moved into the vessel and through the catheter to the treatment site. Typically, this is done by advancing a first, or introduction guidewire, through the vessel to the region of interest. A catheter is advanced over the guidewire to the region of interest, and the guidewire removed. Then the filter or other functional device carried by the elongate support member is advanced down a catheter sheath to the region of interest but within the catheter. The catheter sheath is withdrawn to deploy (expand) the filter at the region of interest. Alternatively, the filter is preloaded into a catheter and held in place by an outer sheath of the catheter and they are together advanced through the vessel to the region of interest without using an initial guidewire. In this embodiment the catheter/filter combination will be used to navigate through the vessel to the region of interest. Then the catheter is withdrawn to deploy the filter.

Typical dimensions of a filter used in the devices of this invention range from 2 nm to 90 mm in length, and from about 0.5 mm to 2 mm in diameter before deployment, and from about 2 mm to 30 mm in diameter after deployment. A typical guidewire is about 0.2 to 1.0 mm in diameter and ranges from 50 cm to 320 cm in length.

The components of the distal protection system are made from biocompatible materials. Materials also may be surface treated to produce biocompatibility. The elongate support member may be formed of any material of suitable dimension, and preferably comprises metal wire. Suitable materials include stainless steel, titanium and its alloys, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, and the like. A shape memory or superelastic metal such as nitinol is also suitable. The elongate support member may be solid or may be hollow over some or all of its length.

The material used to make the filter or filter support structure is preferably self-expanding. Suitable materials include metals such as stainless steel, titanium and its alloys, cobalt-chromium-nickel molybdenum-iron alloy (commercially available under the trade designation Elgiloy™), carbon fiber and its composites, and engineered polymers such as liquid crystal polymers, polyetheretherketone (PEEK), polyimide, polyester, silk, and the like. A shape memory or superelastic metal is particularly suitable for those applications when it is desired for an element, such as a filter, to assume a pre-determined three-dimensional shape or for a guidewire to maintain a pre-determined curvature. A shape memory or superelastic metal comprising nickel and titanium known as "nitinol" is commercially available in various dimensions and is suitable for use as both a guidewire and a filter. For example, nitinol tubular braid can be heat set into a desired shape, compressed for delivery to a site, and then released to resume the heat-set shape.

The filter element has a body defining an interior cavity. The filter body has a plurality of openings or pores such that, when the filter element is in its deployed configuration within the vessel lumen, fluid flows through the filter element and particles of the desired size are captured inside the interior cavity of the filter element.

The filter may comprise any material that is suitably flexible and resilient, such as a mesh, a material having openings or pores. The filter may comprise braided, knitted, woven, or non-woven fabrics that are capable of filtering particles, preferably having pore sizes from 30 to 500 microns. Woven or non-woven fabrics may additionally be treated to fuse some or all of the fiber intersections. The fabric may be spun or electrospun. Suitable materials include those formed from sheets, films, or sponges, polymeric or metallic, with holes formed by mechanical means such as laser drilling and punching, or by chemical means such as selective dissolution of one or more components. For example, a suitable filter material is braided tubular fabric comprising superelastic nitinol metal. Mesh fabric of nitinol material can be heat-set to a desired shape in its expanded configuration.

The material comprising the filter is preferably at least partially radiopaque. This material can be made radiopaque by plating, or by using core wires, tracer wires, or fillers that have good X-ray absorption characteristics compared to the human body. Radiopaque filters are described in U.S. Patent Application Publication No. 2002/0188314 A1, published Dec. 12, 2002, to Anderson et al., the contents of which are hereby incorporated by reference herein.

The embodiments of this invention, described in detail below in connection with the figures, are suitable for use with various distal protection systems that are known in the art. The filter may have a windsock type shape. The construction, deployment and retrieval of a filter having this shape is described, for example, in U.S. Pat. No. 6,325,815 B1, issued Dec. 4, 2001, to Kusleika et al., the contents of which are hereby incorporated by reference herein. Other features of filters relevant to the invention disclosed herein are described in U.S. Pat. No. 6,773,448 B2, issued Aug. 10, 2004, to Kusleika et al., U.S. Patent Application Publication No. 2003/0171771 A1, published Sep. 11, 2003, to Anderson et al., and U.S. Patent Application Publication No. 2004/0153119 A1, published Aug. 5, 2004, to Kusleika et al., the contents of each of which are incorporated herein by reference.

The filter may also be a cup-shaped or basket-shaped device that may form a proximally facing opening when expanded. The construction, deployment, and retrieval of such a filter is described in WO 96/01591 (Mazzocchi et al.). This cup-shaped device may generally resemble an umbrella or a parachute, having a dome-like structure curving radially outwardly from the guidewire or elongate support member. Other shapes may be equally suitable in performing a filtering function, such as a conical shape, or a relatively flat disc shape. It will be appreciated that the shape of these filtration devices shown in various embodiments are merely illustrative and are not meant to limit the scope of the invention.

Regardless of the shape of the filter, the filter preferably is deployed using an elongate support member. This can be done in various ways, and one or both of the proximal and distal ends of the filter may be affixed to the elongate support member (by a fixed element) or may be slidably disposed about the elongate support member (by one or more sliding elements).

One type of sliding element comprises inner and outer annular rings. The first ring fits within the second ring. The inner diameter of the first ring is larger than the diameter of the elongate support member so that the sliding element can slide over the elongate support member. The sliding element can be affixed to the filter fabric by placing the fabric between the first and second rings. However, this is not meant to be limiting, and the filter fabric can also be affixed to the sliding element by adhesive, solder, crimping, or other means known in the art. The sliding element may comprise any stiff material such as metal or polymer and preferably the slider is radiopaque. Suitable materials include stainless steel, titanium, platinum, platinum/iridium alloy, gold alloy, polyimide, polyester, polyetheretherketone (PEEK), and the like. Movement of a sliding element with respect to the elongate support member can be facilitated by coating one or both of the inside of the sliding element and the outside of the elongate support member with a friction-reducing coating, such as polytetrafluoroethylene or a lubricious hydrophilic coating.

Fixed elements include annular rings. Also included within this meaning is an element that is crimped, adhered, soldered, or otherwise fastened directly to the elongate support member. Also, the filter fabric may be attached directly to the elongate support member. In any event, the sliding and fixed elements (or any attachment point) typically comprise radiopaque material to assist in the placement of the filter. In addition, one or more radiopaque markers may be positioned at various locations on the protection device. These radiopaque markers or market bands comprise a material that will be visible to X-rays and they assist in positioning the device.

Some distal protection filters include a floppy tip at a distal portion of the guidewire or elongate support element. The floppy tip provides an atraumatic and radiopaque terminus for the device. An atraumatic tip prevents vessel injury during initial placement or subsequent advancement of the device. A radiopaque tip helps the physician verify suitable tip placement during fluoroscopy. The floppy tip preferably comprises a springy or resilient material, such as a metal (e.g., stainless steel, iron alloys such as Elgiloy™, platinum, gold, tungsten, and shape memory or superelastic metal such as nitinol) or polymer (e.g., polyetheretherketone (PEEK), polyimide, polyester, polytetrafluoroethylene (PTFE), and the like). Springy materials are desirable because they tend to retain their shape. The physician will initially shape the tip, typically with a slight curve, and then as the device is advanced through the body the tip will be deflected as it encounters obstacles. It is desirable, after the inevitable deflections during insertion, that the tip restores itself to the pre-set shape. Polymeric materials additionally may be reinforced with metals or other fillers. The tip may be a monofilament or multifilament (such as a cable). The floppy tip may be tapered or have a uniform diameter over its length. The floppy tip may comprise a tube, or could have circular, flat, or other cross-sections. It may be coiled. The tip may comprise one or more elements (for example, parallel independent structures). The tip may be polymer-coated or otherwise treated to make the surface slippery. The floppy tip can be any desired length.

The filter comprises biocompatible materials such as metals and polymeric materials. Materials such as metals and polymeric materials can be treated to impart biocompatibility by various surface treatments, as known in the art. When wire is used, the wire is selected on the basis of the characteristic desired, i.e., stiffness or flexibility, and the properties can depend upon both the diameter of the wire and its cross-sectional shape. The size, thickness, and composition of elastic materials are selected for their ability to perform as desired as well as their biocompatibility. It is to be understood that these design elements are known to one of skill in the art.

The present invention includes a host wire for an embolic filter device that has a side branch or rail for the filter to be positioned in such a manner that the host wire portion of the device remains centered in the vessel in which the filter is deployed. Various embodiments of the invention are disclosed which include the provision for some type of side branch or rail positioned at or near the distal end of the host wire. This side branch or rail may be created by splitting the distal end of the wire in half or by attaching an additional wire to the main host wire. The wire branch that has been created by this design angles away from the main host wire. A portion of the embolic filter is retained on this side branch resulting in the positioning of the filter to one side of the vessel wall. The angle of the side branch allows the main wire to remain centered in the vessel. This side branch may reattach to the main wire at a more distal location from the main angle separation point. Typically, the filter is configured to move freely longitudinally along this side branch. In addition the side branch may rotate axially around the main wire to allow rotational movement of the main wire without affecting the filter position in the vessel. Thus, the design allows both rotational and longitudinal movement of the host wire without disruption of the position of the deployed filter device within the vessel. This is accomplished by providing in the various embodiments a combination of rotateable, sliding elements and stops. This concept provides for excellent device wall apposition with minimized wire bias and filter movement and maximizes the filtration capabilities of the filter within the vessel.

Figure 11:
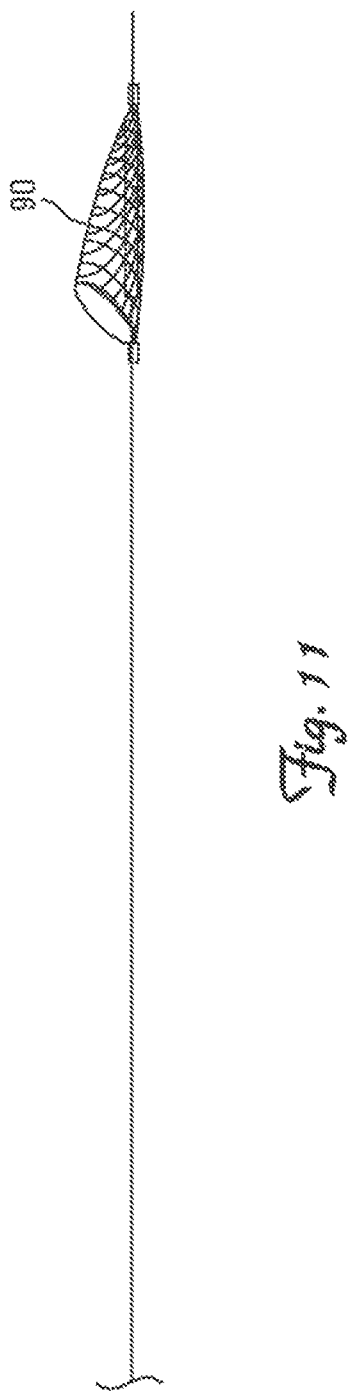
FIG. 11 shows an embolic protection device.

The unproved embolic filter device disclosed herein is used in a manner consistent with embolic filtration devices such as the embolic filter device 90 disclosed in FIG. 11. A potential disadvantage of this filter is that, under certain circumstances, the proximally facing mouth of the filter may not fully open when the filter is deployed. This is because the circumference of the filter mouth is attached to the support wire. Thus, if the support wire is spaced from the vessel wall where the filter is deployed the mouth of the filter may not fully open. The present invention overcomes that problem.

The filter may be preloaded onto the delivery end of the catheter described previously and advanced to the treatment location over the primary guidewire. The guidewire is then removed and filter and host wire advanced and deployed from the distal end of be delivery catheter. The delivery catheter is removed, the primary intervention is performed over the device host wire (for example angioplasty or, stenting) and upon completion of the primary intervention, the recovery catheter end of the previous device is advanced to recover the filter and host wire for removal as described previously. Other delivery catheters, recovery catheters and combined delivery/recovery catheters can also be used.

The improved embolic filter device embodiments disclosed herein act to center the wire within the vessel where the filter is deployed. This prevents wire bias that can cause the filter mouth to collapse or have reduced wall apposition. The design provides minimal obstruction to the entrance of the filter device while allowing the host wire to remain centered in the vessel. Various embodiments of the improved embolic filter device are disclosed in FIGS. 12 to 17.

Figure 12:
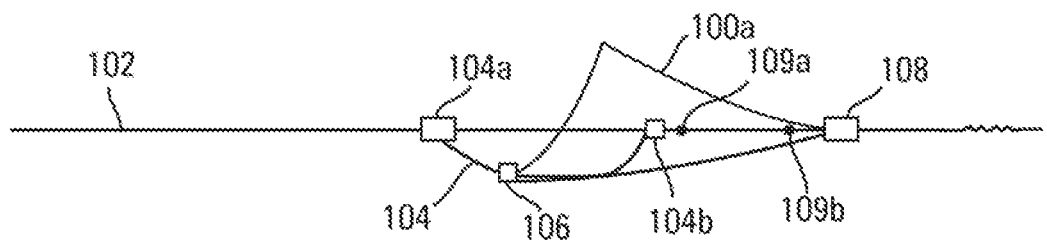
FIGS. 12 to 17 show various embodiments of an embolic filtration device in accordance with the present invention.

FIG. 12 discloses an embolic filter device 100a carried on a host wire 102. Host wire 102 includes a side branch 104, Side branch 104 is rotateably and slideably attached at its ends by sliders 104a and 104b. Embolic filter device 100a has a proximal slider 106 and a distal slider 108. Proximal slider 106 is adapted to slide over side branch 104 while distal slider 108 is adapted to slide over host wire 102. Longitudinal movement of the embolic filter and side branch 104 is limited both proximally and distally by stops 109a and 109b.

Figure 13:
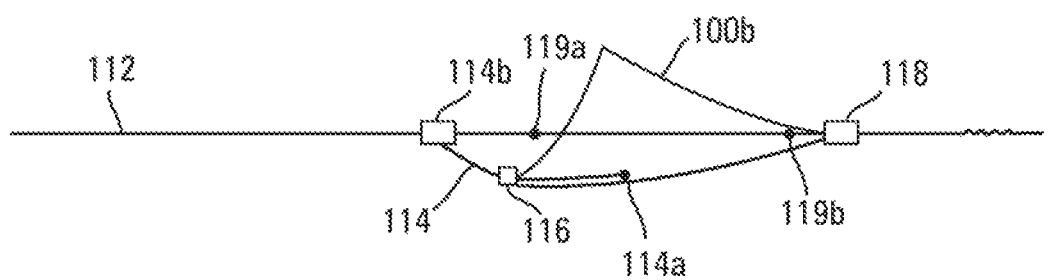

FIG. 13 discloses an embolic filter device 100b which is carried by a host wire 112. Host wire 112 includes a forked portion 114 having a distal stop 114a. Forked portion 114 is connected rotateably and slideably to host wire 112 by slider 114b. Embolic filter device 100b has a proximal slider 116 and a distal slider 118. Proximal slider 116 is configured to slide along fork 114 between its connection point at a proximal end to host wire 112 and distal stop 114a. Distal slider 118 is configured to slide over host wire 112. Longitudinal movement of the embolic filter and forked portion is limited both proximally and distally by stops 119a and 119b.

Figure 14:
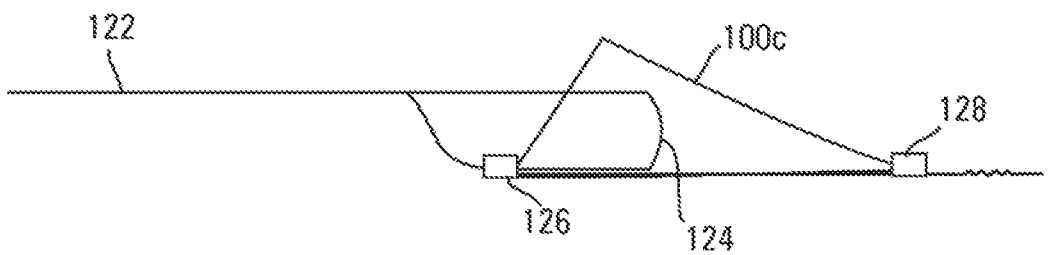

FIG. 14 discloses an embolic filter device 100c carried by a host wire 122. Host wire 122 is provided with a looped portion 124. Embolic filter device 100c has a proximal slider 126 and a distal band 128. Proximal slider 126 of embolic filter device 100c is configured to slide over that portion of the looped portion 124 that is spaced apart from host wire 122. In this embodiment rotation of the host wire 122 cannot be done without affecting the position of filter device 100c.

Figure 15:
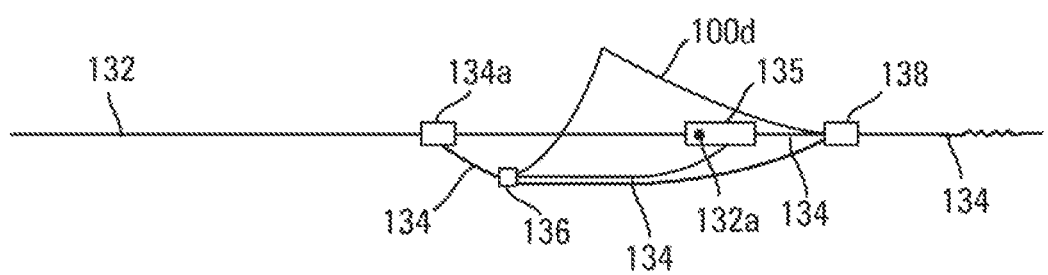

FIG. 15 snows embolic fitter device 100d carried by a host wire 132. Host wire 132 has an enlarged distal end 132a that is indelibly received in a tube 135. Host wire 132 has a branch 134. One end of branch 134 is rotateably and slideably connected to host wire 132 at slider 134a. Embolic protection device 100d has a proximal slider 136 adapted to slide over branch 134 and a distal slider 138 which slides over an extending portion of branch 134. Branch 134 is fixed between its proximal and distal ends to tube 135.

Figure 16:
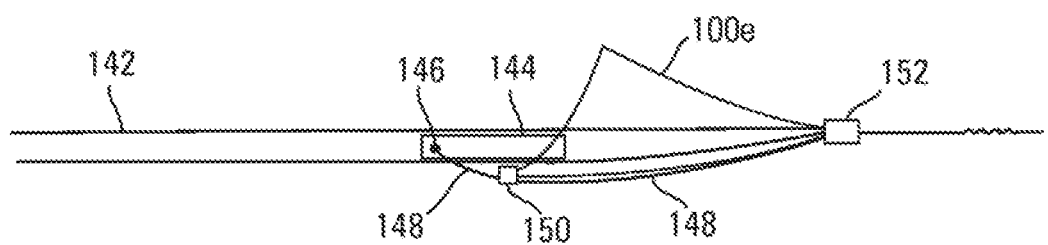

FIG. 16 discloses an embolic filter device 100e carried by host wire 142. Host wire 142 has a slot 144 adapted to receive a sliding element 146. Sliding element 146 is connected by wire 148 to a proximal end 150 of embolic filter device 100e. Wire 148 is sized and shaped to center host wire 142 in the proximal opening of embolic filter device 100e when deployed in a lumen. Embolic filter device 100e includes distal slider 152 which is configured to slide over a distal portion of host wire 142. Host wire 142 is provided with some range of axial movement with respect to embolic filter device 100e by virtue of sliding element 146 and distal slider 152.

Figure 17:
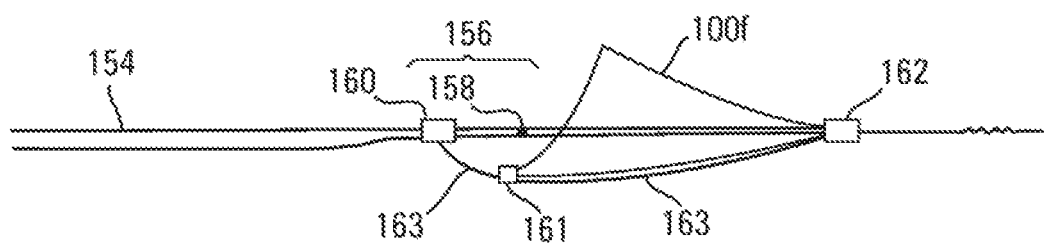

FIG. 17 discloses an embolic filter device 100f carried by host wire 154. Host wire 154 has a tapered portion 156 bounded at a distal end by stop 158. Embolic filter device 100f includes a proximal end 161 which is connected to slider 160 by wire 163. Slider 160 slides over host wire 154 over a range of motion bounded by tapered portion 156 and distal slider 162 slides over a distal portion of host wire 154.

The foregoing detailed description should be read with reference to the drawings and which like elements in different drawings are numbered identically. The drawings, which are not necessarily to scale, depict selected embodiments and are not intended to limit the scope of the invention. Several forms of invention have been shown and described, and other forms will now be apparent to those skilled in the art. It will be understood that embodiments shown in drawings and described above are merely for illustrative purposes, and are not intended to limit the scope of the invention as defined in the claims which follow.

What is claimed is:

1. A system comprising:
    a guidewire;
    a catheter comprising:
        an elongated member configured to be advanced along a vascular path of a patient, the elongated member comprising a proximal portion, a distal portion, a proximal end, a distal end, a housing portion adjacent to and proximal of the distal portion, and a sidewall exit port proximal of the housing portion, the sidewall exit port being dimensioned to receive the guidewire,
        the distal end comprising a distal port,
        the housing portion defining an interior cavity; and
    a housing member contained within the interior cavity, the housing member having an interior space dimensioned for housing an indwelling medical device, and the housing member having a proximal end that is distal of the proximal end of the elongated member, and
    the elongated member comprising a lumen extending at least from the exit port to the distal port, the housing member being disposed within the lumen and the lumen encompassing the interior cavity of the housing portion,
    wherein the guidewire is configured to extend through the distal port, through a portion of the lumen in the housing portion, the portion extending between an interior surface of the housing portion and an exterior surface of the housing member, and through the exit port.

2. The system of claim 1, wherein the housing member is secured at a fixed location within the housing portion.

3. The system of claim 1, wherein the housing member is configured to move axially within the housing portion.

4. The system of claim 3, wherein the housing portion comprises distal and proximal housing sections, and wherein the housing member is configured to move axially between the proximal and distal sections of the housing portion.

5. The system of claim 4, wherein the proximal housing section comprises a stop member.

6. The system of claim 5, wherein the stop member defines one or more sidewall slots configured to define pathways for the guidewire.

7. The system of claim 1, wherein the housing portion and the distal portion have outer diameters and the outer diameter of the housing portion is larger than the outer diameter of the distal portion.

8. The system of claim 1, wherein the housing portion and the distal portion have inner diameters and the inner diameter of the housing portion is larger than the inner diameter of the distal portion.

9. The system of claim 5, wherein the housing portion and the distal portion have inner diameters and the inner diameter of the housing portion is larger than the inner diameter of the distal portion.

10. The system of claim 1, wherein the elongated member comprises an inner wall defining the lumen and the housing member is adjacent to the inner wall.

11. The system of claim 1, wherein the housing member is centered within the lumen.

12. The system of claim 1, wherein the housing member is tubular.

13. The system of claim 1, further comprising a ramp in the lumen configured to direct the guidewire out the exit port when the guidewire is in the lumen.

14. The system of claim 1, wherein the proximal portion comprises an indwelling medical device retrieval structure.

15. The system of claim 1, wherein at least a portion of the housing portion is transparent.

16. The system of claim 1, wherein the proximal end of the elongated member comprises a rolled tip.

17. The system of claim 1, wherein the proximal end of the elongated member comprises a shapeable tip.

18. An assembly comprising a medical device and the system of claim 1, wherein the medical device is configured to be delivered and retrieved by the elongated member.

19. The assembly of claim 18, wherein the medical device comprises an embolic protection device, a balloon catheter, a stent delivery catheter, an atrial appendage occlusion device, a mitral valve remodeling device, or a septal defect closure device.

20. The assembly of claim 18, wherein the medical device is an embolic protection device.

21. The assembly of claim 20, wherein the embolic protection device is a filter.

22. The assembly of claim 20, wherein the embolic protection device is an occlusive device.

23. An assembly comprising the system of claim 1 and a removable packaging sheath having an end adapted to accommodate a fluid filled syringe for flushing the elongated member.

24. A method for positioning a medical device within a patient's blood vessel, the method comprising:
placing the medical device within a housing member contained within an interior cavity of a catheter, the catheter comprising:
an elongated member configured to be advanced along a vascular path of a patient, the elongated member comprising a proximal portion, a distal portion, a proximal end, a distal end, a housing portion adjacent to and proximal of the distal portion, and a sidewall exit port proximal of the housing portion, the sidewall exit port being dimensioned to receive the guidewire,
the distal end comprising a distal port,
the housing portion defining the interior cavity,
the elongated member comprising a lumen extending at least from the exit port to the distal port, the housing member being disposed within the lumen and the lumen encompassing the interior cavity of the housing portion, the housing member having a proximal end that is distal of the proximal end of the elongated member;
advancing the catheter to a target site within the patient's blood vessel over a guidewire, the guidewire extending through the distal port, through a portion of the lumen in the housing portion, the portion extending between an interior surface of the housing portion and an exterior surface of the housing member, and through the exit port; and
advancing the medical device out of the catheter to the target site within the patient's blood vessel.

25. A method for positioning a catheter within a patient's blood vessel, the method comprising:
advancing a guidewire to a target site within the patient's blood vessel; and
advancing a catheter over the guidewire, the catheter comprising:
an elongated member configured to be advanced along a vascular path of a patient, the elongated member comprising a proximal portion, a distal portion, a proximal end, a distal end, a housing portion adjacent to and proximal of the distal portion, and a sidewall exit port proximal of the housing portion, the sidewall exit port being dimensioned to receive the guidewire,
the distal end comprising a distal port,
the housing portion defining the interior cavity,
the elongated member comprising a lumen extending at least from the exit port to the distal port, a housing member being disposed within the lumen and the lumen encompassing the interior cavity of the housing portion, the housing member having a proximal end that is distal of the proximal end of the elongated member,
wherein advancing the catheter over the guidewire comprises inserting the guidewire through the lumen between the distal port and the sidewall exit port, such that the guidewire extends through the distal port, through a portion of the lumen in the housing portion, the portion extending between an interior surface of the housing portion and an exterior surface of the housing member, and through the exit port.

26. The method of claim 25, wherein an embolic protection device is loaded into the catheter prior to advancing the catheter over the guidewire.

27. The method of claim 26, wherein the catheter is advanced over the guidewire to a treatment site, the guidewire is removed, and the embolic protection device is advanced out of the catheter.

* * * * *